(12) United States Patent
Dooley

(10) Patent No.: US 10,140,887 B2
(45) Date of Patent: Nov. 27, 2018

(54) BRAILLE GENERATOR AND CONVERTER

(71) Applicant: Pearson Education, Inc., New York, NY (US)

(72) Inventor: Samuel Sean Dooley, Alburquerque, NM (US)

(73) Assignee: PEARSON EDUCATION, INC., New York, NY (US)

( * ) Notice: Subject to any disclaimer, the term of this patent is extended or adjusted under 35 U.S.C. 154(b) by 0 days.

(21) Appl. No.: 14/856,860

(22) Filed: Sep. 17, 2015

(65) Prior Publication Data

US 2017/0084201 A1    Mar. 23, 2017

(51) Int. Cl.
*G09B 21/00* (2006.01)
*A61F 9/08* (2006.01)

(52) U.S. Cl.
CPC .......... *G09B 21/003* (2013.01); *A61F 9/08* (2013.01)

(58) Field of Classification Search
CPC .............................. G09B 21/003; A61F 9/08
USPC ........................................................ 434/117
See application file for complete search history.

(56) References Cited

U.S. PATENT DOCUMENTS

| | | | | |
|---|---|---|---|---|
| 2007/0136334 A1* | 6/2007 | Schleppenbach | ..... | G06F 17/215 |
| 2010/0299150 A1* | 11/2010 | Fein | ..... | G06F 17/289 |
| | | | | 704/277 |
| 2011/0020771 A1* | 1/2011 | Rea | ..... | G09B 21/02 |
| | | | | 434/114 |
| 2013/0173247 A1* | 7/2013 | Hodson | ..... | G06F 17/2827 |
| | | | | 704/4 |
| 2015/0213723 A1* | 7/2015 | Vattikonda | ..... | G09B 5/00 |
| | | | | 434/322 |

* cited by examiner

*Primary Examiner* — Michael Grant
(74) *Attorney, Agent, or Firm* — Kilpatrick Townsend and Stockton LLP

(57) ABSTRACT

Techniques described herein relate to generating braille output and/or visual display output based on received mathematical expression input. Data corresponding to one or more mathematical expressions may be received via expression input devices or visual display devices, and may be converted to braille output characters for display on refreshable braille devices. Additionally, mathematical expression input data may be received via refreshable braille display devices and converted to output characters for display on visual display devices. In some embodiments, mathematical expression input data may be converted first to content markup, and then converted from the content markup to presentation markup and/or braille output characters. Further mathematical expression input data, such as updates to previously displayed expressions, may be received from an initial input device, visual display device, or refreshable braille device, and the updated expression data may be converted to visual output characters and/or braille output characters.

18 Claims, 15 Drawing Sheets

Content Markup for Mathematical Expression 2x + (3y) / 4

```
<math xmlns="http://www.w3.org/1998/Math/MathML">
    <apply>
        <plus/>
        <apply>
            <times/>
            <cn>2</cn>
            <ci>x</ci>
        </apply>
        <apply>
            <divide/>
            <apply>
                <times/>
                <cn>3</cn>
                <ci>y</ci>
            </apply>
            <cn>4</cn>
        </apply>
    </apply>
</math>
```

FIG. 10A

Presentation Markup for Mathematical Expression 2x + (3y) / 4

```
<math xmlns="http://www.w3.org/1998/Math/MathML">
    <mrow>
        <mrow>
            <mn>2</mn>
            <mo>⁢</mo>
            <mi>x</mi>
        </mrow>
        <mo>+</mo>
        <mfrac>
            <mrow>
                <mn>3</mn>
                <mo>⁢</mo>
                <mi>y</mi>
            </mrow>
            <mn>4</mn>
        </mfrac>
    </mrow>
</math>
```

FIG. 10B

Content Markup for Mathematical Expression
x = (-b pm sqrt( b^2 - 4ac ) ) / ( 2a )

```
<math xmlns="http://www.w3.org/1998/Math/MathML">
    <apply>
        <eq/>
        <ci>x</ci>
        <apply>
            <divide/>
            <apply>
                <plus/>
                <apply>
                    <minus/>
                    <ci>b</ci>
                </apply>
                <apply>
                    <pm/>
                    <apply>
                        <root/>
                        <apply>
                            <plus/>
                            <apply>
                                <power/>
                                <ci>b</ci>
                                <cn>2</cn>
                            </apply>
                            <apply>
                                <minus/>
                                <apply>
                                    <times/>
                                    <cn>4</cn>
                                    <ci>a</ci>
                                    <ci>c</ci>
                                </apply>
                            </apply>
                        </apply>
                    </apply>
                </apply>
            </apply>
            <apply>
                <times/>
                <cn>2</cn>
                <ci>a</ci>
            </apply>
        </apply>
    </apply>
</math>
```

FIG. 11A

Presentation Markup for Mathematical Expression
x = (-b pm sqrt( b^2 - 4ac ) ) / ( 2a )

```
<math xmlns="http://www.w3.org/1998/Math/MathML">
    <mrow>
        <mi>x</mi>
        <mo>=</mo>
        <mfrac>
            <mrow>
                <mrow>
                    <mo>-</mo>
                    <mi>b</mi>
                </mrow>
                <mrow>
                    <mo form="infix">±</mo>
                    <msqrt>
                        <mrow>
                            <msup>
                                <mi>b</mi>
                                <mn>2</mn>
                            </msup>
                            <mrow>
                                <mo form="infix">-</mo>
                                <mrow>
                                    <mn>4</mn>
                                    <mo>⁢</mo>
                                    <mi>a</mi>
                                    <mo>⁢</mo>
                                    <mi>c</mi>
                                </mrow>
                            </mrow>
                        </mrow>
                    </msqrt>
                </mrow>
            </mrow>
            <mrow>
                <mn>2</mn>
                <mo>⁢</mo>
                <mi>a</mi>
            </mrow>
        </mfrac>
    </mrow>
</math>
```

FIG. 11B

BRAILLE GENERATOR AND CONVERTER

BACKGROUND

A number of computing devices and technologies are available for visually impaired users who are unable to read monitors and other visual display screens. For example, refreshable braille display devices may include a number of electromechanical braille cells having output pins that may be raised or lowered to form braille characters. Such devices also may include braille keyboards to allow for braille readers to input data. Additional devices used by visually impaired users may include devices having microphones and voice recognition and control functionality for receiving input, as well as device speakers and speech synthesizers for generating audio rather than visual output.

BRIEF SUMMARY

Various techniques are described herein for generating visual display output and/or braille output based on received mathematical expression input. In certain embodiments, data corresponding to one or more mathematical expressions may be received via expression input devices or visual display devices, and may be converted to braille output characters for display on one or more refreshable braille devices. Additionally, mathematical expression input data may be received via one or more refreshable braille display devices and converted to output characters for display on visual display devices. In some embodiments, mathematical expression input data may be converted first to content markup, and then converted from the content markup to presentation markup and/or braille output characters. Further mathematical expression input data, such as updates to previously displayed expressions, may be received from an initial input device, visual display device, or refreshable braille device, and the updated expression data may be converted to visual output characters and/or braille output characters.

In certain techniques described herein, at least four separate data converters and/or conversion processes may be supported to perform four separate expression conversions, including a mathematical expression input to content markup converter and/or conversion process, a braille character input to content markup converter and/or conversion process, a content markup to braille output character converter and/or conversion process, and/or a content markup to presentation markup converter and/or conversion process. In some embodiments, each mathematical expression converter and/or conversion process may use separate sets of conversion rules, including character mapping rules as well as various special encoding and decoding rules for mathematical expressions. Additionally, in certain embodiments, some or all of the converters and/or conversion processes may be initiated in real-time or near real-time in response to receiving a single-character input or revision to a mathematical expression from a visual display device or a refreshable braille terminal. The implementation of these embodiments and other embodiments described herein may provide support for multi-user viewing, editing, and other collaborative work involving mathematical expression data, where such multi-user collaboration may occur simultaneously and without expression ambiguity, for combinations of sighted users interacting via visual display devices and visually impaired users interacting via refreshable braille display devices.

BRIEF DESCRIPTION OF THE DRAWINGS

FIGS. 10A and 10B show samples of content markup and presentation markup representing an example mathematical expression, according to one or more embodiments of the disclosure.

FIGS. 11A and 11B show samples of content markup and presentation markup representing another example mathematical expression, according to one or more embodiments of the disclosure.

Figure 1:
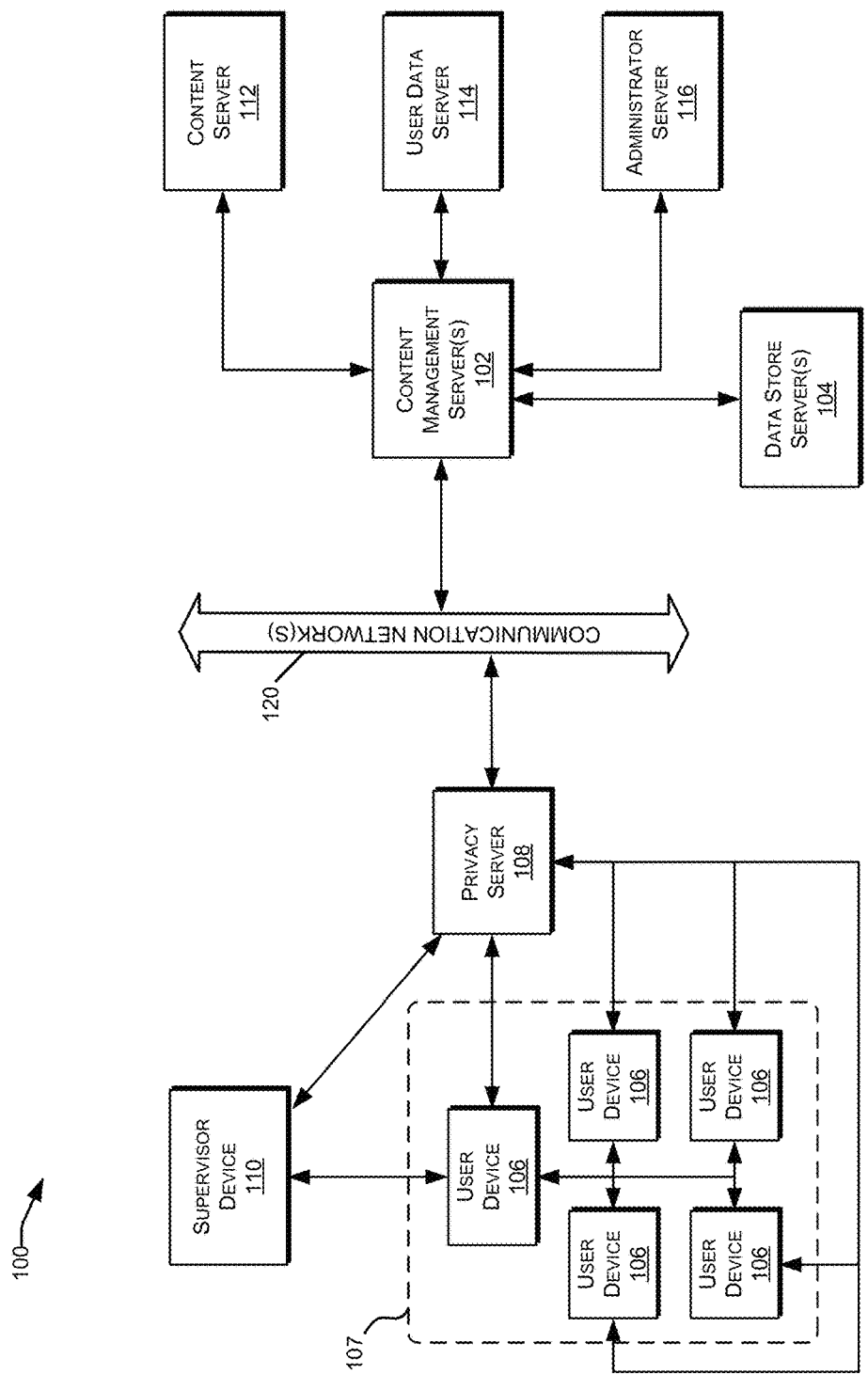
FIG. 1 is a block diagram showing illustrating an example of a content distribution network.

In the appended figures, similar components and/or features may have the same reference label. Further, various compo of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides illustrative embodiment(s) only and is not intended to limit the scope, applicability or configuration of the disclosure. Rather, the ensuing description of the illustrative embodiment(s) will provide those skilled in the art with an enabling description for implementing a preferred exemplary embodiment. It is understood that various changes can be made in the function and arrangement of elements without departing from the spirit and scope as set forth in the appended claims.

Various techniques (e.g., systems, methods, computer-program products tangibly embodied in a non-transitory computer-readable storage medium, etc.) are described herein for generating visual display output and/or braille output based on received mathematical expression input. In certain examples described herein, data corresponding to one or more mathematical expressions may be received via expression input devices or visual display devices, and may be converted to braille output characters for display on a refreshable braille device. Additionally, mathematical expression input data may be received via one or more refreshable braille display devices and converted to output characters for display on visual display devices. In some embodiments, mathematical expression input data may be converted first to content markup, and then converted from the content markup to presentation markup and/or braille output characters. Further mathematical expression input data, such as updates to previously displayed expressions, may be received from an initial input device, visual display device, or refreshable braille device, and the updated expression data may be converted to visual output characters and/or braille output characters.

In accordance with certain techniques described herein, at least four separate data converters and/or conversion processes may be supported to perform four separate expression conversions, including a mathematical expression input to content markup converter and/or conversion process, a braille character input to content markup converter and/or conversion process, a content markup to braille output character converter and/or conversion process, and/or a content markup to presentation markup converter and/or conversion process. In some embodiments, each mathematical expression converter and/or conversion process may use separate sets of conversion rules, including various special encoding and decoding rules for mathematical expressions that do not correspond to character mapping rules. Additionally, in certain embodiments, some or all of the converters and/or conversion processes may be initiated in real-time or near real-time in response to receiving a single-character input or revision to a mathematical expression from a visual display device or a refreshable braille terminal. The implementation of these embodiments and other embodiments described herein may provide support for multi-user viewing, editing, and other collaborative work involving mathematical expression data, where such multi-user collaboration may occur simultaneously and without expression ambiguity, for combinations of sighted users interacting via visual display devices and visually impaired users interacting via refreshable braille display devices.

With reference now to FIG. 1, a block diagram is shown illustrating various components of a content distribution network (CDN) 100 which implements and supports certain embodiments and features described herein. Content distribution network 100 may include one or more content management servers 102. As discussed below in more detail, content management servers 102 may be any desired type of server including, for example, a rack server, a tower server, a miniature server, a blade server, a mini rack server, a mobile server, an ultra-dense server, a super server, or the like, and may include various hardware components, for example, a motherboard, a processing units, memory systems, hard drives, network interfaces, power supplies, etc. Content management server 102 may include one or more server farms, clusters, or any other appropriate arrangement and/or combination or computer servers. Content management server 102 may act according to stored instructions located in a memory subsystem of the server 102, and may run an operating system, including any commercially available server operating system and/or any other operating systems discussed herein.

The content distribution network 100 may include one or more data store servers 104, such as database servers and file-based storage systems. Data stores 104 may comprise stored data relevant to the functions of the content distribution network 100. Illustrative examples of data stores 104 that may be maintained in certain embodiments of the content distribution network 100 are described below in reference to FIG. 3. In some embodiments, multiple data stores may reside on a single server 104, either using the same storage components of server 104 or using different physical storage components to assure data security and integrity between data stores. In other embodiments, each data store may have a separate dedicated data store server 104.

Content distribution network 100 also may include one or more user devices 106 and/or supervisor devices 110. User devices 106 and supervisor devices 110 may display content received via the content distribution network 100, and may support various types of user interactions with the content. User devices 106 and supervisor devices 110 may include mobile devices such as smartphones, tablet computers, personal digital assistants, and wearable computing devices. Such mobile devices may run a variety of mobile operating systems, and may be enabled for Internet, e-mail, short message service (SMS), Bluetooth®, mobile radio-frequency identification (M-RFID), and/or other communication protocols. Other user devices 106 and supervisor devices 110 may be general purpose personal computers or special-purpose computing devices including, by way of example, personal computers, laptop computers, workstation computers, projection devices, and interactive room display systems. Additionally, user devices 106 and supervisor devices 110 may be any other electronic devices, such as thin-client computers, Internet-enabled gaming systems, business or home appliances, and/or personal messaging devices, capable of communicating over network(s) 120.

In different contexts of content distribution networks 100, user devices 106 and supervisor devices 110 may correspond to different types of specialized devices, for example, student devices and teacher devices in an educational network, employee devices and presentation devices in a company network, different gaming devices in a gaming network, etc. In some embodiments, user devices 106 and supervisor devices 110 may operate in the same physical location 107, such as a classroom or conference room. In such cases, the devices may contain components that support direct communications with other nearby devices, such as a wireless transceivers and wireless communications interfaces, Ethernet sockets or other Local Area Network (LAN) interfaces, etc. In other implementations, the user devices 106 and supervisor devices 110 need not be used at the same location 107, but may be used in remote geographic locations in which each user device 106 and supervisor device 110 may use security features and/or specialized hardware (e.g., hardware-accelerated SSL and HTTPS, WS-Security, firewalls, etc.) to communicate with the content management server 102 and/or other remotely located user devices 106. Additionally, different user devices 106 and supervisor devices 110 may be assigned different designated roles, such as presenter devices, teacher devices, administrator devices, or the like, and in such cases the different devices may be provided with additional hardware and/or software components to provide content and support user capabilities not available to the other devices.

The content distribution network 100 also may include a privacy server 108 that maintains private user information at the privacy server 108 while using applications or services hosted on other servers. For example, the privacy server 108 may be used to maintain private data of a user within one jurisdiction even though the user is accessing an application hosted on a server (e.g., the content management server 102) located outside the jurisdiction. In such cases, the privacy server 108 may intercept communications between a user device 106 or supervisor device 110 and other devices that include private user information. The privacy server 108 may create a token or identifier that does not disclose the private information and may use the token or identifier when communicating with the other servers and systems, instead of using the user's private information.

As illustrated in FIG. 1, the content management server 102 may be in communication with one or more additional servers, such as a content server 112, a user data server 112, and/or an administrator server 116. Each of these servers may include some or all of the same physical and logical components as the content management server(s) 102, and in some cases, the hardware and software components of these servers 112-116 may be incorporated into the content management server(s) 102, rather than being implemented as separate computer servers.

Content server 112 may include hardware and software components to generate, store, and maintain the content resources for distribution to user devices 106 and other devices in the network 100. For example, in content distribution networks 100 used for professional training and educational purposes, content server 112 may include data stores of training materials, presentations, interactive programs and simulations, course models, course outlines, and various training interfaces that correspond to different materials and/or different types of user devices 106. In content distribution networks 100 used for media distribution, interactive gaming, and the like, a content server 112 may include media content files such as music, movies, television programming, games, and advertisements.

User data server 114 may include hardware and software components that store and process data for multiple users relating to each user's activities and usage of the content distribution network 100. For example, the content management server 102 may record and track each user's system usage, including their user device 106, content resources accessed, and interactions with other user devices 106. This data may be stored and processed by the user data server 114, to support user tracking and analysis features. For instance, in the professional training and educational contexts, the user data server 114 may store and analyze each user's training materials viewed, presentations attended, courses completed, interactions, evaluation results, and the like. The user data server 114 may also include a repository for user-generated material, such as evaluations and tests completed by users, and documents and assignments prepared by users. In the context of media distribution and interactive gaming, the user data server 114 may store and process resource access data for multiple users (e.g., content titles accessed, access times, data usage amounts, gaming histories, user devices and device types, etc.).

Administrator server 116 may include hardware and software components to initiate various administrative functions at the content management server 102 and other components within the content distribution network 100. For example, the administrator server 116 may monitor device status and performance for the various servers, data stores, and/or user devices 106 in the content distribution network 100. When necessary, the administrator server 116 may add or remove devices from the network 100, and perform device maintenance such as providing software updates to the devices in the network 100. Various administrative tools on the administrator server 116 may allow authorized users to set user access permissions to various content resources, monitor resource usage by users and devices 106, and perform analyses and generate reports on specific network users and/or devices (e.g., resource usage tracking reports, training evaluations, etc.).

The content distribution network 100 may include one or more communication networks 120. Although only a single network 120 is identified in FIG. 1, the content distribution network 100 may include any number of different communication networks between any of the computer servers and devices shown in FIG. 1 and/or other devices described herein. Communication networks 120 may enable communication between the various computing devices, servers, and other components of the content distribution network 100. As discussed below, various implementations of content distribution networks 100 may employ different types of networks 120, for example, computer networks, telecommunications networks, wireless networks, and/or any combination of these and/or other networks.

Figure 2:
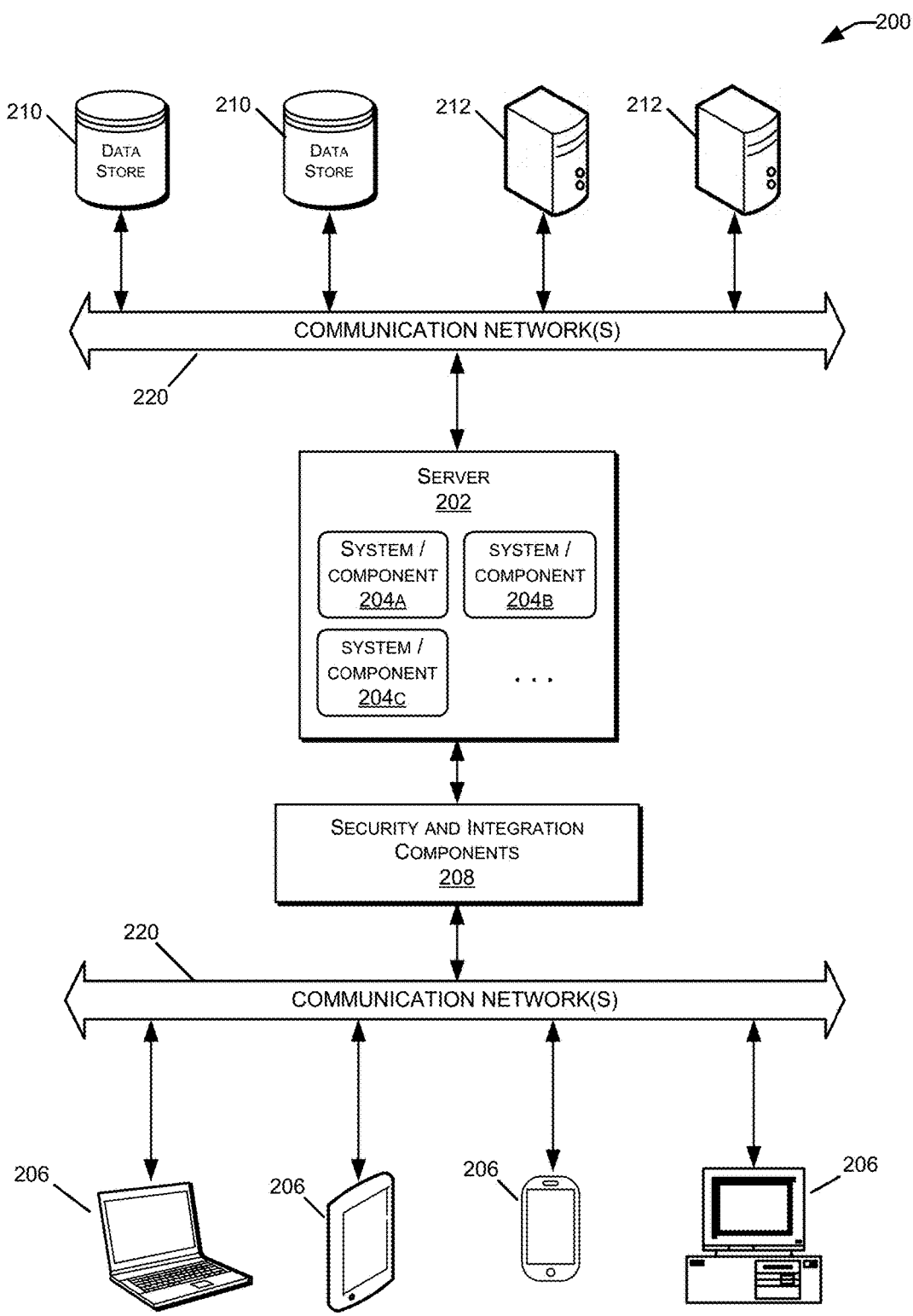
FIG. 2 is a block diagram illustrating a computer server and computing environment within a content distribution network.

With reference to FIG. 2, an illustrative distributed computing environment 200 is shown including a computer server 202, four client computing devices 206, and other components that may implement certain embodiments and features described herein. In some embodiments, the server 202 may correspond to the content management server 102 discussed above in FIG. 1, and the client computing devices 206 may correspond to the user devices 106. However, the computing environment 200 illustrated in FIG. 2 may correspond to any other combination of devices and servers configured to implement a client-server model or other distributed computing architecture.

Client devices 206 may be configured to receive and execute client applications over one or more networks 220. Such client applications may be web browser based applications and/or standalone software applications, such as mobile device applications. Server 202 may be communicatively coupled with the client devices 206 via one or more communication networks 220. Client devices 206 may receive client applications from server 202 or from other application providers (e.g., public or private application stores). Server 202 may be configured to run one or more server software applications or services, for example, web-based or cloud-based services, to support content distribution and interaction with client devices 206. Users operating client devices 206 may in turn utilize one or more client applications (e.g., virtual client applications) to interact with server 202 to utilize the services provided by these components.

Various different subsystems and/or components 204 may be implemented on server 202. Users operating the client devices 206 may initiate one or more client applications to use services provided by these subsystems and components. The subsystems and components within the server 202 and client devices 206 may be implemented in hardware, firmware, software, or combinations thereof. Various different system configurations are possible in different distributed computing systems 200 and content distribution networks 100. The embodiment shown in FIG. 2 is thus one example of a distributed computing system and is not intended to be limiting.

Although exemplary computing environment 200 is shown with four client computing devices 206, any number of client computing devices may be supported. Other devices, such as specialized sensor devices, etc., may interact with client devices 206 and/or server 202.

As shown in FIG. 2, various security and integration components 208 may be used to send and manage communications between the server 202 and user devices 206 over one or more communication networks 220. The security and integration components 208 may include separate servers, such as web servers and/or authentication servers, and/or specialized networking components, such as firewalls, routers, gateways, load balancers, and the like. In some cases, the security and integration components 208 may correspond to a set of dedicated hardware and/or software operating at the same physical location and under the control of same entities as server 202. For example, components 208 may include one or more dedicated web servers and network hardware in a datacenter or a cloud infrastructure. In other examples, the security and integration components 208 may correspond to separate hardware and software components which may be operated at a separate physical location and/or by a separate entity.

Security and integration components 208 may implement various security features for data transmission and storage, such as authenticating users and restricting access to unknown or unauthorized users. In various implementations, security and integration components 208 may provide, for example, a file-based integration scheme or a service-based integration scheme for transmitting data between the various devices in the content distribution network 100. Security and integration components 208 also may use secure data transmission protocols and/or encryption for data transfers, for example, File Transfer Protocol (FTP), Secure File Transfer Protocol (SFTP), and/or Pretty Good Privacy (PGP) encryption.

In some embodiments, one or more web services may be implemented within the security and integration components 208 and/or elsewhere within the content distribution network 100. Such web services, including cross-domain and/or cross-platform web services, may be developed for enterprise use in accordance with various web service standards, such as the Web Service Interoperability (WS-I) guidelines. For example, some web services may use the Secure Sockets Layer (SSL) or Transport Layer Security (TLS) protocol to provide secure connections between the server 202 and user devices 206. SSL or TLS may use HTTP or HTTPS to provide authentication and confidentiality. In other examples, web services may be implemented using the WS-Security standard, which provides for secure SOAP messages using XML encryption. In other examples, the security and integration components 208 may include specialized hardware for providing secure web services. For example, security and integration components 208 may include secure network appliances having built-in features such as hardware-accelerated SSL and HTTPS, WS-Security, and firewalls. Such specialized hardware may be installed and configured in front of any web servers, so that any external devices may communicate directly with the specialized hardware.

Communication network(s) 220 may be any type of network familiar to those skilled in the art that can support data communications using any of a variety of commercially-available protocols, including without limitation, TCP/IP (transmission control protocol/Internet protocol), SNA (systems network architecture), IPX (Internet packet exchange), Secure Sockets Layer (SSL) or Transport Layer Security (TLS) protocols, Hyper Text Transfer Protocol (HTTP) and Secure Hyper Text Transfer Protocol (HTTPS), and the like. Merely by way of example, network(s) 220 may be local area networks (LAN), such as one based on Ethernet, Token-Ring and/or the like. Network(s) 220 also may be wide-area networks, such as the Internet. Networks 220 may include telecommunication networks such as a public switched telephone networks (PSTNs), or virtual networks such as an intranet or an extranet. Infrared and wireless networks (e.g., using the Institute of Electrical and Electronics (IEEE) 802.11 protocol suite or other wireless protocols) also may be included in networks 220.

Computing environment 200 also may include one or more data stores 210 and/or back-end servers 212. In certain examples, the data stores 210 may correspond to data store server(s) 104 discussed above in FIG. 1, and back-end servers 212 may correspond to the various back-end servers 112-116. Data stores 210 and servers 212 may reside in the same datacenter or may operate at a remote location from server 202. In some cases, one or more data stores 210 may reside on a non-transitory storage medium within the server 202. Other data stores 210 and back-end servers 212 may be remote from server 202 and configured to communicate with server 202 via one or more networks 220. In certain embodiments, data stores 210 and back-end servers 212 may reside in a storage-area network (SAN).

Figure 3:
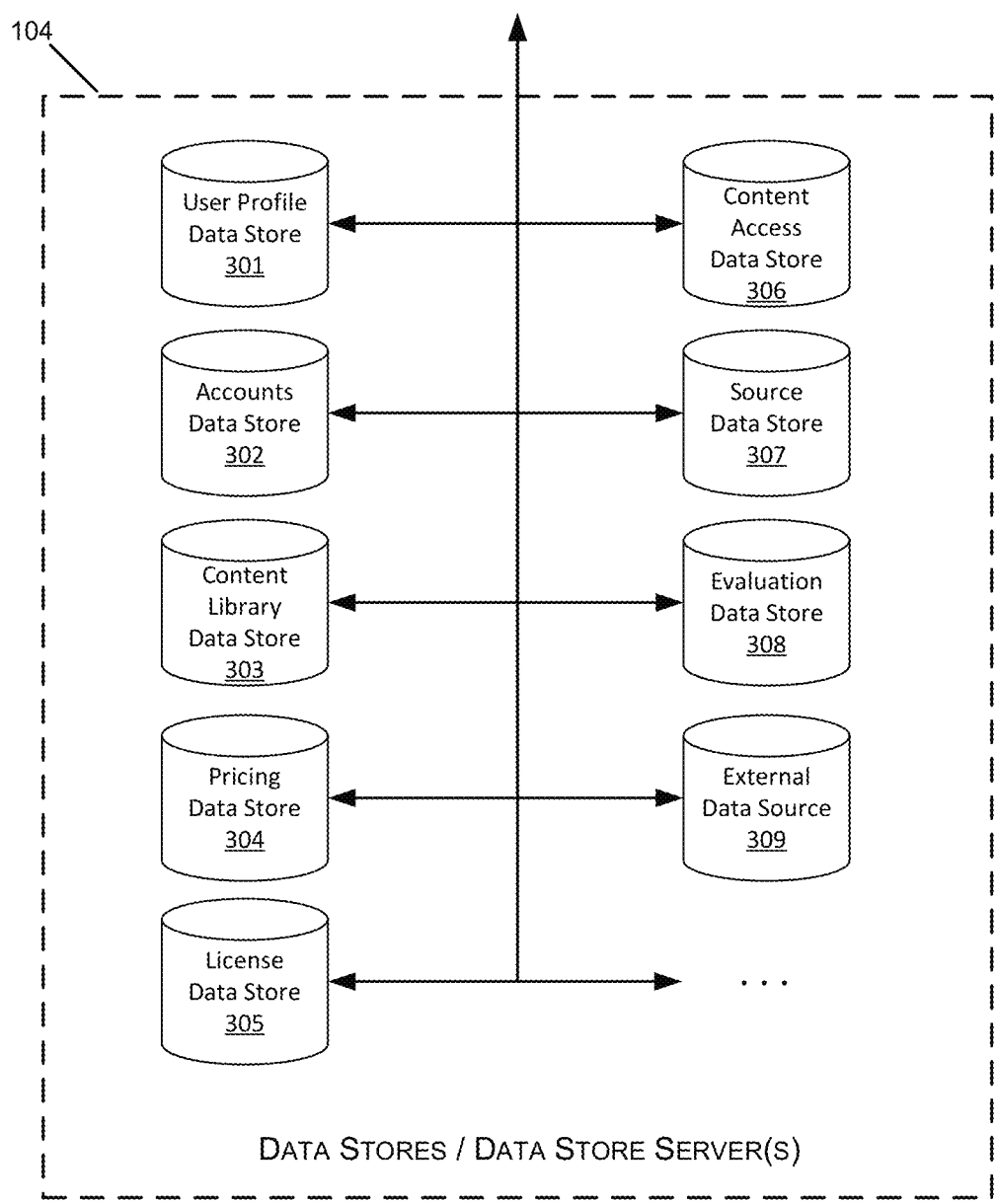
FIG. 3 is a block diagram illustrating an embodiment of one or more data store servers within a content distribution network.

With reference to FIG. 3, an illustrative set of data stores and/or data store servers is shown, corresponding to the data store servers 104 of the content distribution network 100 discussed above in FIG. 1. One or more individual data stores 301-309 may reside in storage on a single computer server 104 (or a single server farm or cluster) under the control of a single entity, or may reside on separate servers operated by different entities and/or at remote locations. In some embodiments, data stores 301-309 may be accessed by the content management server 102 and/or other devices and servers within the network 100 (e.g., user devices 106, supervisor devices 110, administrator servers 116, etc.). Access to one or more of the data stores 301-309 may be limited or denied based on the processes, user credentials, and/or devices attempting to interact with the data store.

The paragraphs below describe examples of specific data stores that may be implemented within some embodiments of a content distribution network 100. It should be understood that the below descriptions of data stores 301-309, including their functionality and types of data stored therein, are illustrative and non-limiting. Data stores server architecture, design, and the execution of specific data stores 301-309 may depend on the context, size, and functional requirements of a content distribution network 100. For example, in content distribution systems 100 used for professional training and educational purposes, separate databases or file-based storage systems may be implemented in data store server(s) 104 to store trainee and/or student data, trainer and/or professor data, training module data and content descriptions, training results, evaluation data, and the like. In contrast, in content distribution systems 100 used for media distribution from content providers to subscribers, separate data stores may be implemented in data stores server(s) 104 to store listings of available content titles and descriptions, content title usage statistics, subscriber profiles, account data, payment data, network usage statistics, etc.

A user profile data store 301 may include information relating to the end users within the content distribution network 100. This information may include user characteristics such as the user names, access credentials (e.g., logins and passwords), user preferences, and information relating to any previous user interactions within the content distribution network 100 (e.g., requested content, posted content, content modules completed, training scores or evaluations, other associated users, etc.).

An accounts data store 302 may generate and store account data for different users in various roles within the content distribution network 100. For example, accounts may be created in an accounts data store 302 for individual end users, supervisors, administrator users, and entities such as companies or educational institutions. Account data may include account types, current account status, account characteristics, and any parameters, limits, restrictions associated with the accounts.

A content library data store 303 may include information describing the individual content items (or content resources) available via the content distribution network 100. In some embodiments, the library data store 303 may include metadata, properties, and other characteristics associated with the content resources stored in the content server 112. Such data may identify one or more aspects or content attributes of the associated content resources, for example, subject matter, access level, or skill level of the content resources, license attributes of the content resources (e.g., any limitations and/or restrictions on the licensable use and/or distribution of the content resource), price attributes of the content resources (e.g., a price and/or price structure for determining a payment amount for use or distribution of the content resource), rating attributes for the content resources (e.g., data indicating the evaluation or effectiveness of the content resource), and the like. In some embodiments, the library data store 303 may be configured to allow updating of content metadata or properties, and to allow the addition and/or removal of information relating to the content resources.

A pricing data store 304 may include pricing information and/or pricing structures for determining payment amounts for providing access to the content distribution network 100 and/or the individual content resources within the network 100. In some cases, pricing may be determined based on a user's access to the content distribution network 100, for example, a time-based subscription fee, or pricing based on network usage and. In other cases, pricing may be tied to specific content resources. Certain content resources may have associated pricing information, whereas other pricing determinations may be based on the resources accessed, the profiles and/or accounts of the user, and the desired level of access (e.g., duration of access, network speed, etc.). Additionally, the pricing data store 304 may include information relating to compilation pricing for groups of content resources, such as group prices and/or price structures for groupings of resources.

A license data store 305 may include information relating to licenses and/or licensing of the content resources within the content distribution network 100. For example, the license data store 305 may identify licenses and licensing terms for individual content resources and/or compilations of content resources in the content server 112, the rights holders for the content resources, and/or common or large-scale right holder information such as contact information for rights holders of content not included in the content server 112.

A content access data store 306 may include access rights and security information for the content distribution network 100 and specific content resources. For example, the content access data store 306 may include login information (e.g., user identifiers, logins, passwords, etc.) that can be verified during user login attempts to the network 100. The content access data store 306 also may be used to store assigned user roles and/or user levels of access. For example, a user's access level may correspond to the sets of content resources and/or the client or server applications that the user is permitted to access. Certain users may be permitted or denied access to certain applications and resources based on their subscription level, training program, course/grade level, etc. Certain users may have supervisory access over one or more end users, allowing the supervisor to access all or portions of the end user's content, activities, evaluations, etc. Additionally, certain users may have administrative access over some users and/or some applications in the content management network 100, allowing such users to add and remove user accounts, modify user access permissions, perform maintenance updates on software and servers, etc.

A source data store 307 may include information relating to the source of the content resources available via the content distribution network. For example, a source data store 307 may identify the authors and originating devices of content resources, previous pieces of data and/or groups of data originating from the same authors or originating devices, and the like.

An evaluation data store 308 may include information used to direct the evaluation of users and content resources in the content management network 100. In some embodiments, the evaluation data store 308 may contain, for example, the analysis criteria and the analysis guidelines for evaluating users (e.g., trainees/students, gaming users, media content consumers, etc.) and/or for evaluating the content resources in the network 100. The evaluation data store 308 also may include information relating to evaluation processing tasks, for example, the identification of users and user devices 106 that have received certain content resources or accessed certain applications, the status of evaluations or evaluation histories for content resources, users, or applications, and the like. Evaluation criteria may be stored in the evaluation data store 308 including data and/or instructions in the form of one or several electronic rubrics or scoring guides for use in the evaluation of the content, users, or applications. The evaluation data store 308 also may include past evaluations and/or evaluation analyses for users, content, and applications, including relative rankings, characterizations, explanations, and the like.

In addition to the illustrative data stores described above, data store server(s) 104 (e.g., database servers, file-based storage servers, etc.) may include one or more external data aggregators 309. External data aggregators 309 may include third-party data sources accessible to the content management network 100, but not maintained by the content management network 100. External data aggregators 309 may include any electronic information source relating to the users, content resources, or applications of the content distribution network 100. For example, external data aggregators 309 may be third-party data stores containing demographic data, education related data, consumer sales data, health related data, and the like. Illustrative external data aggregators 309 may include, for example, social networking web servers, public records data stores, learning management systems, educational institution servers, business servers, consumer sales data stores, medical record data stores, etc. Data retrieved from various external data aggregators 309 may be used to verify and update user account information, suggest user content, and perform user and content evaluations.

Figure 4:
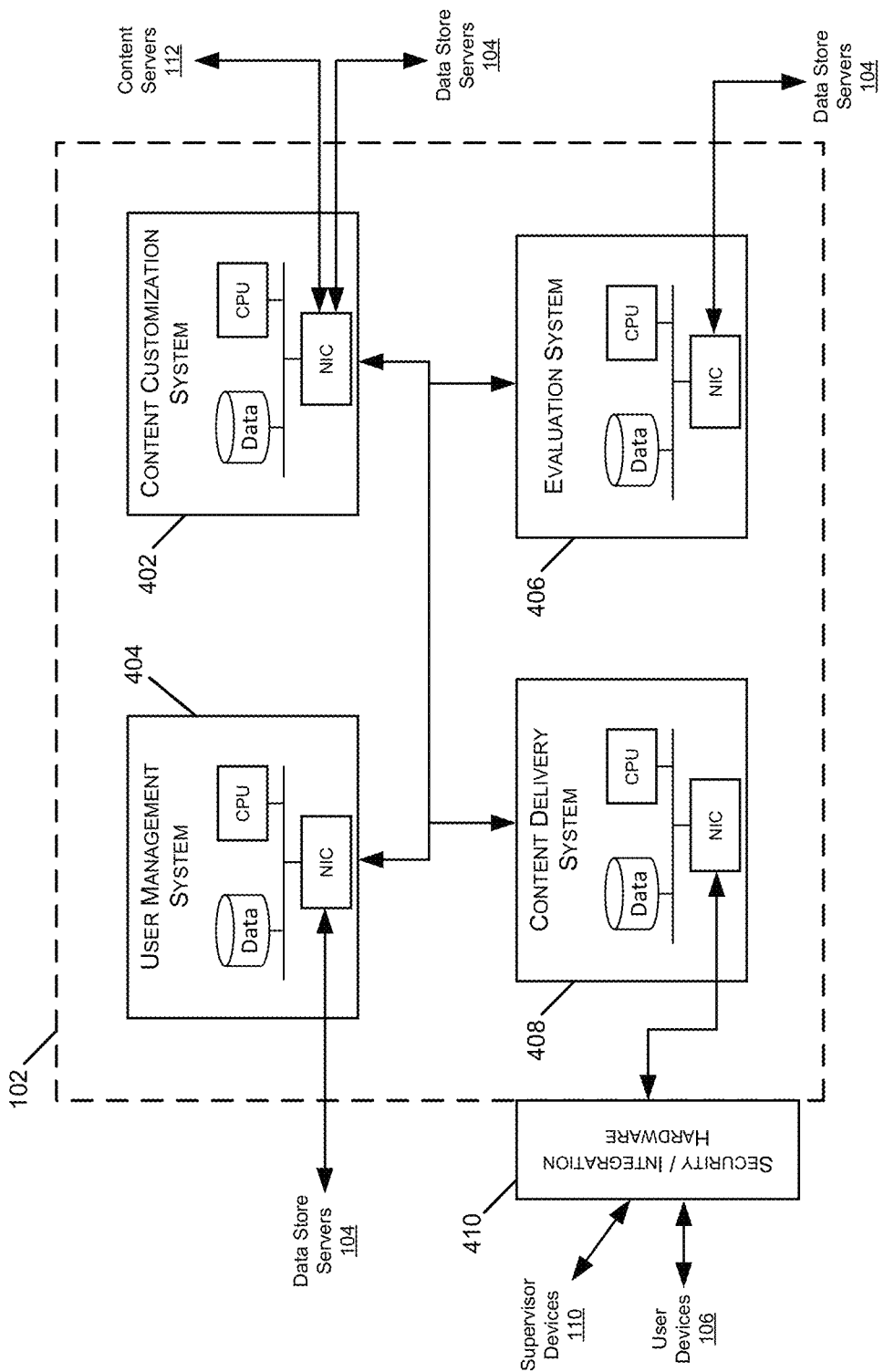
FIG. 4 is a block diagram illustrating an embodiment of one or more content management servers within a content distribution network.

With reference now to FIG. 4, a block diagram is shown illustrating an embodiment of one or more content management servers 102 within a content distribution network 100.

As discussed above, content management server(s) 102 may include various server hardware and software components that manage the content resources within the content distribution network 100 and provide interactive and adaptive content to users on various user devices 106. For example, content management server(s) 102 may provide instructions to and receive information from the other devices within the content distribution network 100, in order to manage and transmit content resources, user data, and server or client applications executing within the network 100.

A content management server 102 may include a content customization system 402. The content customization system 402 may be implemented using dedicated hardware within the content distribution network 100 (e.g., a content customization server 402), or using designated hardware and software resources within a shared content management server 102. In some embodiments, the content customization system 402 may adjust the selection and adaptive capabilities of content resources to match the needs and desires of the users receiving the content. For example, the content customization system 402 may query various data stores and servers 104 to retrieve user information, such as user preferences and characteristics (e.g., from a user profile data store 301), user access restrictions to content recourses (e.g., from a content access data store 306), previous user results and content evaluations (e.g., from an evaluation data store 308), and the like. Based on the retrieved information from data stores 104 and other data sources, the content customization system 402 may modify content resources for individual users.

A content management server 102 also may include a user management system 404. The user management system 404 may be implemented using dedicated hardware within the content distribution network 100 (e.g., a user management server 404), or using designated hardware and software resources within a shared content management server 102. In some embodiments, the user management system 404 may monitor the progress of users through various types of content resources and groups, such as media compilations, courses or curriculums in training or educational contexts, interactive gaming environments, and the like. For example, the user management system 404 may query one or more databases and/or data store servers 104 to retrieve user data such as associated content compilations or programs, content completion status, user goals, results, and the like.

A content management server 102 also may include an evaluation system 406. The evaluation system 406 may be implemented using dedicated hardware within the content distribution network 100 (e.g., an evaluation server 406), or using designated hardware and software resources within a shared content management server 102. The evaluation system 406 may be configured to receive and analyze information from user devices 106. For example, various ratings of content resources submitted by users may be compiled and analyzed, and then stored in a data store (e.g., a content library data store 303 and/or evaluation data store 308) associated with the content. In some embodiments, the evaluation server 406 may analyze the information to determine the effectiveness or appropriateness of content resources with, for example, a subject matter, an age group, a skill level, or the like. In some embodiments, the evaluation system 406 may provide updates to the content customization system 402 or the user management system 404, with the attributes of one or more content resources or groups of resources within the network 100. The evaluation system 406 also may receive and analyze user evaluation data from user devices 106, supervisor devices 110, and administrator servers 116, etc. For instance, evaluation system 406 may receive, aggregate, and analyze user evaluation data for different types of users (e.g., end users, supervisors, administrators, etc.) in different contexts (e.g., media consumer ratings, trainee or student comprehension levels, teacher effectiveness levels, gamer skill levels, etc.).

A content management server 102 also may include a content delivery system 408. The content delivery system 408 may be implemented using dedicated hardware within the content distribution network 100 (e.g., a content delivery server 408), or using designated hardware and software resources within a shared content management server 102. The content delivery system 408 may receive content resources from the content customization system 402 and/or from the user management system 404, and provide the resources to user devices 106. The content delivery system 408 may determine the appropriate presentation format for the content resources based on the user characteristics and preferences, and/or the device capabilities of user devices 106. If needed, the content delivery system 408 may convert the content resources to the appropriate presentation format and/or compress the content before transmission. In some embodiments, the content delivery system 408 may also determine the appropriate transmission media and communication protocols for transmission of the content resources.

In some embodiments, the content delivery system 408 may include specialized security and integration hardware 410, along with corresponding software components to implement the appropriate security features content transmission and storage, to provide the supported network and client access models, and to support the performance and scalability requirements of the network 100. The security and integration layer 410 may include some or all of the security and integration components 208 discussed above in FIG. 2, and may control the transmission of content resources and other data, as well as the receipt of requests and content interactions, to and from the user devices 106, supervisor devices 110, administrative servers 116, and other devices in the network 100.

Figure 5:
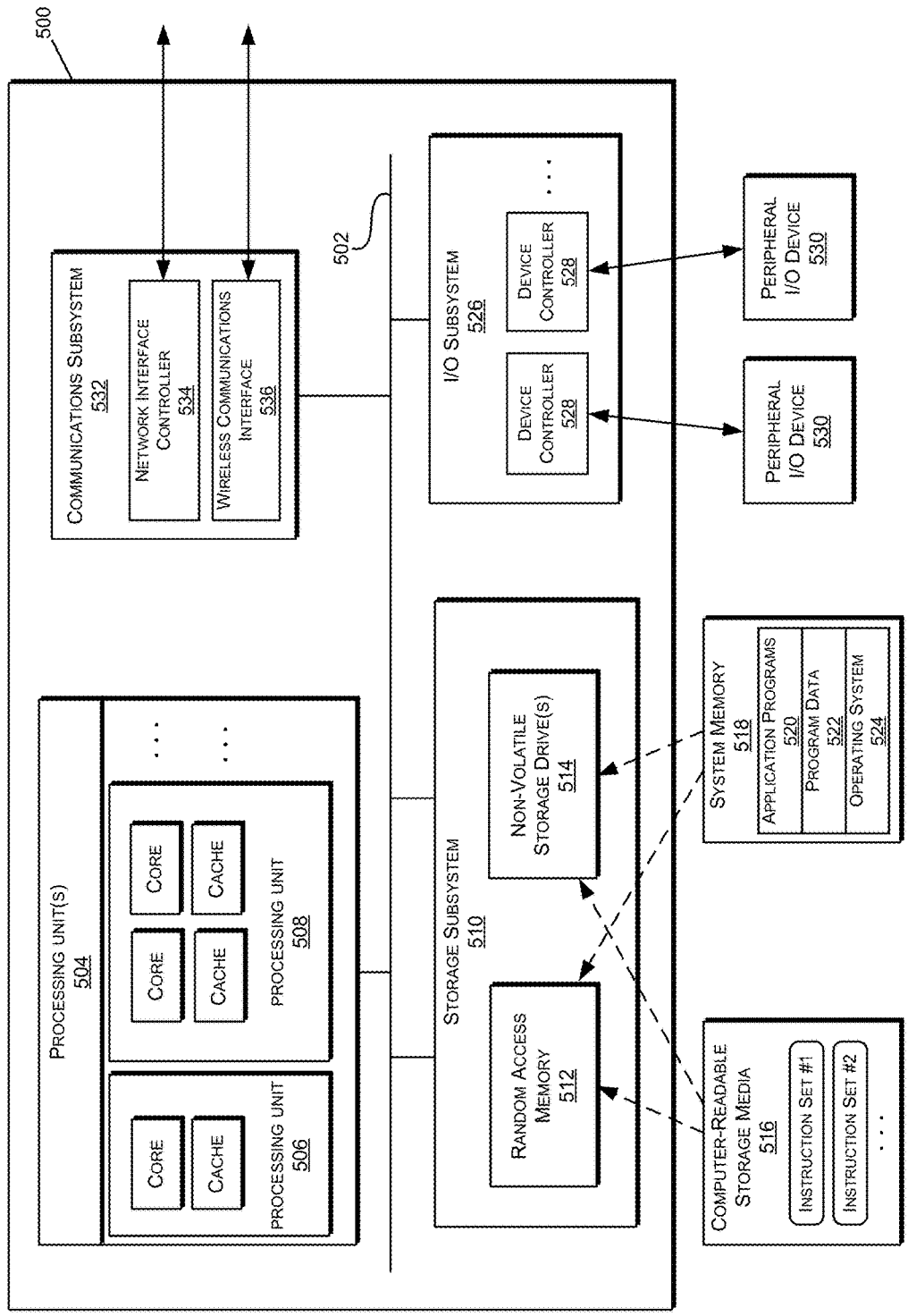
FIG. 5 is a block diagram illustrating the physical and logical components of a special-purpose computer device within a content distribution network.

With reference now to FIG. 5, a block diagram of an illustrative computer system is shown. The system 500 may correspond to any of the computing devices or servers of the content distribution network 100 described above, or any other computing devices described herein. In this example, computer system 500 includes processing units 504 that communicate with a number of peripheral subsystems via a bus subsystem 502. These peripheral subsystems include, for example, a storage subsystem 510, an I/O subsystem 526, and a communications subsystem 532.

Bus subsystem 502 provides a mechanism for letting the various components and subsystems of computer system 500 communicate with each other as intended. Although bus subsystem 502 is shown schematically as a single bus, alternative embodiments of the bus subsystem may utilize multiple buses. Bus subsystem 502 may be any of several types of bus structures including a memory bus or memory controller, a peripheral bus, and a local bus using any of a variety of bus architectures. Such architectures may include, for example, an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which can be implemented as a Mezzanine bus manufactured to the IEEE P1386.1 standard.

Processing unit 504, which may be implemented as one or more integrated circuits (e.g., a conventional microprocessor or microcontroller), controls the operation of computer system 500. One or more processors, including single core and/or multicore processors, may be included in processing unit 504. As shown in the figure, processing unit 504 may be implemented as one or more independent processing units 506 and/or 508 with single or multicore processors and processor caches included in each processing unit. In other embodiments, processing unit 504 may also be implemented as a quad-core processing unit or larger multicore designs (e.g., hexa-core processors, octo-core processors, ten-core processors, or greater.

Processing unit 504 may execute a variety of software processes embodied in program code, and may maintain multiple concurrently executing programs or processes. At any given time, some or all of the program code to be executed can be resident in processor(s) 504 and/or in storage subsystem 510. In some embodiments, computer system 500 may include one or more specialized processors, such as digital signal processors (DSPs), outboard processors, graphics processors, application-specific processors, and/or the like.

I/O subsystem 526 may include device controllers 528 for one or more user interface input devices and/or user interface output devices 530. User interface input and output devices 530 may be integral with the computer system 500 (e.g., integrated audio/video systems, and/or touchscreen displays), or may be separate peripheral devices which are attachable/detachable from the computer system 500.

Input devices 530 may include a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. Input devices 530 may also include three dimensional (3D) mice, joysticks or pointing sticks, gamepads and graphic tablets, and audio/visual devices such as speakers, digital cameras, digital camcorders, portable media players, webcams, image scanners, fingerprint scanners, barcode reader 3D scanners, 3D printers, laser rangefinders, and eye gaze tracking devices. Additional input devices 530 may include, for example, motion sensing and/or gesture recognition devices that enable users to control and interact with an input device through a natural user interface using gestures and spoken commands, eye gesture recognition devices that detect eye activity from users and transform the eye gestures as input into an input device, voice recognition sensing devices that enable users to interact with voice recognition systems through voice commands, medical imaging input devices, MIDI keyboards, digital musical instruments, and the like.

Output devices 530 may include one or more display subsystems, indicator lights, or non-visual displays such as audio output devices, etc. Display subsystems may include, for example, cathode ray tube (CRT) displays, flat-panel devices, such as those using a liquid crystal display (LCD) or plasma display, projection devices, touch screens, and the like. In general, use of the term "output device" is intended to include all possible types of devices and mechanisms for outputting information from computer system 500 to a user or other computer. For example, output devices 530 may include, without limitation, a variety of display devices that visually convey text, graphics and audio/video information such as monitors, printers, speakers, headphones, automotive navigation systems, plotters, voice output devices, and modems.

Computer system 500 may comprise one or more storage subsystems 510, comprising hardware and software components used for storing data and program instructions, such as system memory 518 and computer-readable storage media 516. The system memory 518 and/or computer-readable storage media 516 may store program instructions that are loadable and executable on processing units 504, as well as data generated during the execution of these programs.

Depending on the configuration and type of computer system 500, system memory 318 may be stored in volatile memory (such as random access memory (RAM) 512) and/or in non-volatile storage drives 514 (such as read-only memory (ROM), flash memory, etc.) The RAM 512 may contain data and/or program modules that are immediately accessible to and/or presently being operated and executed by processing units 504. In some implementations, system memory 518 may include multiple different types of memory, such as static random access memory (SRAM) or dynamic random access memory (DRAM). In some implementations, a basic input/output system (BIOS), containing the basic routines that help to transfer information between elements within computer system 500, such as during start-up, may typically be stored in the non-volatile storage drives 514. By way of example, and not limitation, system memory 518 may include application programs 520, such as client applications, Web browsers, mid-tier applications, server applications, etc., program data 522, and an operating system 524.

Storage subsystem 510 also may provide one or more tangible computer-readable storage media 516 for storing the basic programming and data constructs that provide the functionality of some embodiments. Software (programs, code modules, instructions) that when executed by a processor provide the functionality described herein may be stored in storage subsystem 510. These software modules or instructions may be executed by processing units 504. Storage subsystem 510 may also provide a repository for storing data used in accordance with the present invention.

Storage subsystem 300 may also include a computer-readable storage media reader that can further be connected to computer-readable storage media 516. Together and, optionally, in combination with system memory 518, computer-readable storage media 516 may comprehensively represent remote, local, fixed, and/or removable storage devices plus storage media for temporarily and/or more permanently containing, storing, transmitting, and retrieving computer-readable information.

Computer-readable storage media 516 containing program code, or portions of program code, may include any appropriate media known or used in the art, including storage media and communication media, such as but not limited to, volatile and non-volatile, removable and non-removable media implemented in any method or technology for storage and/or transmission of information. This can include tangible computer-readable storage media such as RAM, ROM, electronically erasable programmable ROM (EEPROM), flash memory or other memory technology, CD-ROM, digital versatile disk (DVD), or other optical storage, magnetic cassettes, magnetic tape, magnetic disk storage or other magnetic storage devices, or other tangible computer readable media. This can also include nontangible computer-readable media, such as data signals, data transmissions, or any other medium which can be used to transmit the desired information and which can be accessed by computer system 500.

By way of example, computer-readable storage media 516 may include a hard disk drive that reads from or writes to non-removable, nonvolatile magnetic media, a magnetic disk drive that reads from or writes to a removable, non-volatile magnetic disk, and an optical disk drive that reads from or writes to a removable, nonvolatile optical disk such as a CD ROM, DVD, and Blu-Ray® disk, or other optical media. Computer-readable storage media 516 may include, but is not limited to, Zip® drives, flash memory cards, universal serial bus (USB) flash drives, secure digital (SD) cards, DVD disks, digital video tape, and the like. Computer-readable storage media 516 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magnetoresistive RAM (MRAM) SSDs, and hybrid SSDs that use a combination of DRAM and flash memory based SSDs. The disk drives and their associated computer-readable media may provide non-volatile storage of computer-readable instructions, data structures, program modules, and other data for computer system 500.

Communications subsystem 532 may provide a communication interface from computer system 500 and external computing devices via one or more communication networks, including local area networks (LANs), wide area networks (WANs) (e.g., the Internet), and various wireless telecommunications networks. As illustrated in FIG. 5, the communications subsystem 532 may include, for example, one or more network interface controllers (NICs) 534, such as Ethernet cards, Asynchronous Transfer Mode NICs, Token Ring NICs, and the like, as well as one or more wireless communications interfaces 536, such as wireless network interface controllers (WNICs), wireless network adapters, and the like. Additionally and/or alternatively, the communications subsystem 532 may include one or more modems (telephone, satellite, cable, ISDN), synchronous or asynchronous digital subscriber line (DSL) units, FireWire® interfaces, USB® interfaces, and the like. Communications subsystem 536 also may include radio frequency (RF) transceiver components for accessing wireless voice and/or data networks (e.g., using cellular telephone technology, advanced data network technology, such as 3G, 4G or EDGE (enhanced data rates for global evolution), WiFi (IEEE 802.11 family standards, or other mobile communication technologies, or any combination thereof), global positioning system (GPS) receiver components, and/or other components.

The various physical components of the communications subsystem 532 may be detachable components coupled to the computer system 500 via a computer network, a FireWire® bus, or the like, and/or may be physically integrated onto a motherboard of the computer system 500. Communications subsystem 532 also may be implemented in whole or in part by software.

In some embodiments, communications subsystem 532 may also receive input communication in the form of structured and/or unstructured data feeds, event streams, event updates, and the like, on behalf of one or more users who may use or access computer system 500. For example, communications subsystem 532 may be configured to receive data feeds in real-time from users of social networks and/or other communication services, web feeds such as Rich Site Summary (RSS) feeds, and/or real-time updates from one or more third party information sources (e.g., data aggregators 309). Additionally, communications subsystem 532 may be configured to receive data in the form of continuous data streams, which may include event streams of real-time events and/or event updates (e.g., sensor data applications, financial tickers, network performance measuring tools, clickstream analysis tools, automobile traffic monitoring, etc.). Communications subsystem 532 may output such structured and/or unstructured data feeds, event streams, event updates, and the like to one or more data stores 104 that may be in communication with one or more streaming data source computers coupled to computer system 500.

Due to the ever-changing nature of computers and networks, the description of computer system 500 depicted in the figure is intended only as a specific example. Many other configurations having more or fewer components than the system depicted in the figure are possible. For example, customized hardware might also be used and/or particular elements might be implemented in hardware, firmware, software, or a combination. Further, connection to other computing devices, such as network input/output devices, may be employed. Based on the disclosure and teachings provided herein, a person of ordinary skill in the art will appreciate other ways and/or methods to implement the various embodiments.

Figure 6:
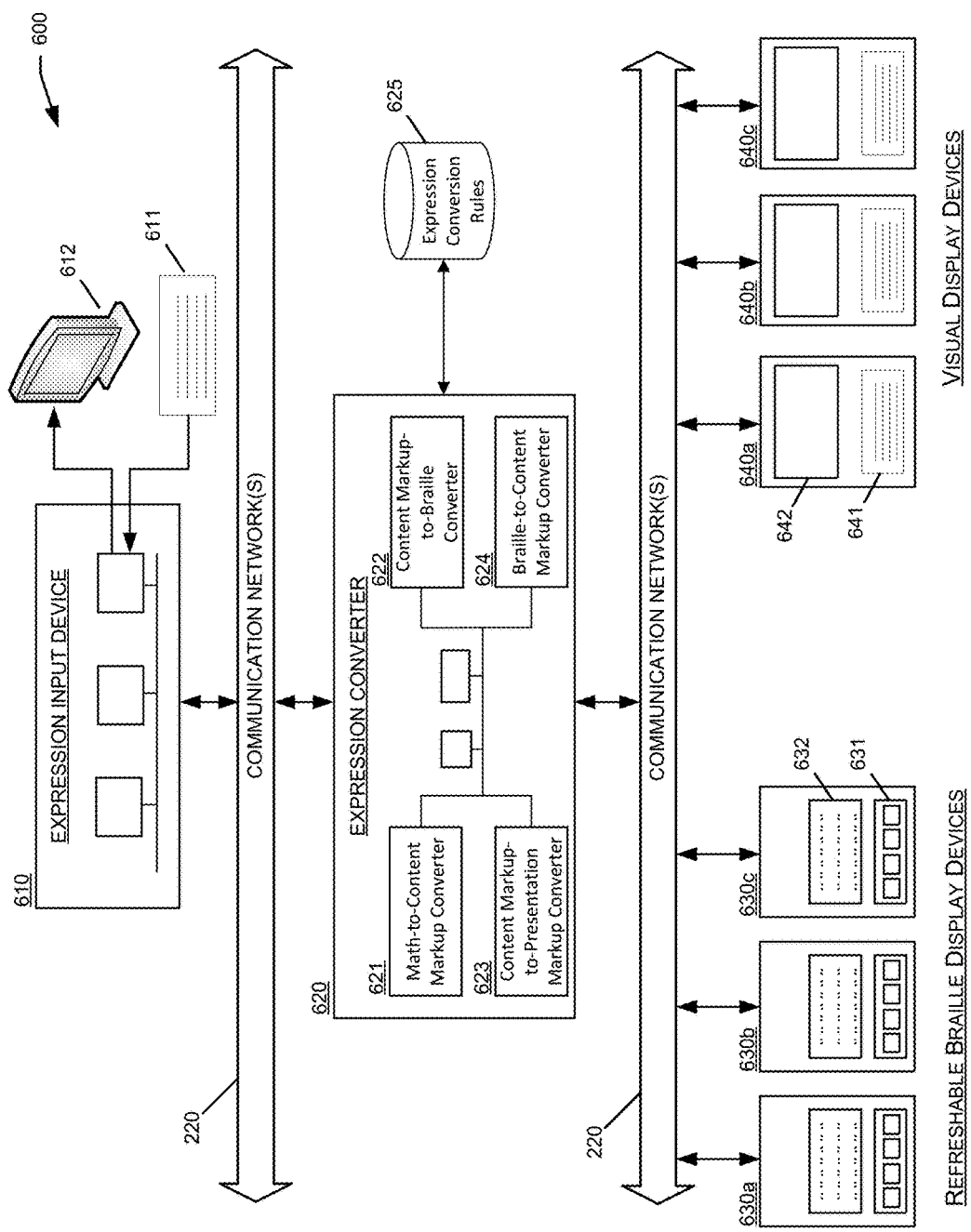
FIG. 6 is a block diagram illustrating an example system for converting and generating braille mathematical expression output and visual mathematical expression output, according to one or more embodiments of the disclosure.

With reference now to FIG. 6, a block diagram is shown illustrating an example of a mathematical expression conversion system 600. In various implementations, an expression conversion system 600 may include one or more expression input devices 610, refreshable braille display devices 630, and/or visual display devices 640, each of which may include or may be configured to communicate with an expression converter 620. As discussed below, the devices and components discussed in reference to system 600 may receive and parse input corresponding to various different types of mathematical expressions, perform one or more conversions on the received mathematical expressions, and then generate braille and/or visual output representing the mathematical expressions via the refreshable braille display devices 630 and/or visual display devices 640. More specifically, in various embodiments, expression input devices 610, refreshable braille display devices 630, and visual display devices 640 may be configured to receive, parse, and transmit data corresponding to inputs of mathematical expressions, as well as receive and output converted mathematical expressions using braille output characters and/or visual output characters. Expression converters 620 may be configured to receive mathematical expression input data, perform various conversions on the input data, and then output converted mathematical expressions to various appropriate user devices 410, 430, and 440. Such conversions may include, for example, mathematical expression input to content markup conversions, braille character input to content markup conversions, content markup to braille character output conversions, and content markup to presentation markup conversions.

In order to perform these features and other functionality described herein, each of the components and sub-components discussed in the example mathematical expression conversion system 600 may correspond to a single computer server or a complex computing system including a combination of computing devices, storage devices, network components, etc. Each of these components and their respective subcomponents may be implemented in hardware, software, or a combination thereof. Certain expression input devices 610, refreshable braille display devices 630, and/or visual display devices 640 may communicate directly with the expression converter 620, while other such devices may communicate with the expression converter 620 indirectly via one or more intermediary network components (e.g., routers, gateways, firewalls, etc.) or other devices in a content distribution network (e.g., content management servers 102, content servers 112, etc.). Although the physical components of communication networks 220 have not been shown in this figure so as not to obscure the other elements depicted in the figure, it should be understood that any of the network hardware components and network architecture designs may be implemented in various embodiments to support communication between the servers, devices, and data stores in the system 600. Additionally, different devices 610, 630, and/or 640 may use different networks and networks types to communicate with each other and with the expression converter 620, including one or more telecommunications networks, cable networks, satellite networks, cellular networks and other wireless networks, and computer-based IP networks, and the like. Further, certain components within mathematical expression conversion system 600 may include special purpose hardware devices and/or special purpose software, such as those included in I/O subsystems of expression input devices 610, refreshable braille display devices 630, and/or visual display devices 640, in order to receive, parse, render, and display various mathematical expressions using braille or visual output characters. Additional special purpose hardware devices and/or special purpose software may be included within the processing units and memory systems of the expression converter 620 and/or devices 610, 630, and 640, in order to parse, store, and convert various types of special and non-standard mathematical characters and symbols, and complex mathematical expressions.

The mathematical expression conversion system 600, and other examples and embodiments described herein, may be used to receive input data corresponding to mathematical expressions, parse and convert the received expressions, and output braille and visual character representations of the expressions on various display devices. As used herein, a mathematical expression may be any expression containing one or more mathematical symbols, including numbers, variables, operators, and functions, as well as grouping symbols and any other mathematical symbol. Different types of mathematical expressions that may be received, converted, generated, and/or output in the various embodiments described herein may include arithmetic expressions, algebraic expressions, polynomial expressions, closed-form expressions, and the like. Examples of specific mathematical expressions may include any combination of one or more constants, variables, arithmetic operators, factorials, exponents, roots, logarithms, trigonometric functions, integrals, differentials, and the like. Moreover, it should be understood that these specific examples and the other examples of mathematical expressions described herein are illustrative only and non-limiting, and that the techniques described herein may be used to receive, parse, convert, and generate braille and/or visual output for any mathematical expression.

In some embodiments, mathematical expression conversion systems 600 may be integrated within, or configured to operate in collaboration with, one or more content distribution networks 100. For example, system 600 may be the same as, or may operate within or in collaboration with, any of the content distribution network (CDNs) 100 described above. Thus, specific implementations of a mathematical expression conversion system 600 may include, without limitation, educational and professional training systems and networks, interactive gaming systems and networks, presentation systems and networks, collaborative working systems and networks, websites and other Internet-based systems and networks, etc. In such cases, expression converters 620 may be implemented within one or more content servers 112, content management servers 102, and/or data store servers 104, and expression input devices 610, refreshable braille display devices 630, and visual display devices 640 correspond to the user devices 106 and 110 described above in reference to CDN 100. In other examples, expression converter 620 may be implemented using one or more computer servers, and other specialized hardware and software components, separately from other CDN components such as content servers 112, content management servers 102, data store servers 104, and the like. In these examples, the expression converter 620 may be configured to communicate directly with devices 610, 630, and 640, or indirectly through content management servers 102 and/or other components and communications networks of a CDN 100.

Expression input devices 610 may include any computing device configured to receive user input corresponding to a mathematical expression. Thus, expression input devices 610 may include desktop and laptop computers, smartphones, tablet computers, mobile devices, and the like. As shown in this example, certain expression input devices 610 may include one or more input components 611 and/or output components 612, which may be peripheral devices which are attachable/detachable from the from the device 610, or may be integrated within the device 610. Input components 611 may include, for example, keyboards, mouses, styluses, touchscreen displays, cameras, microphones, etc. Output components 612 may include various display screens, audio and/or video systems, etc. In some cases, expression input devices 610 may include specialized hardware components and/or software components for inputting and outputting mathematical expressions. For instance, an expression input device 610 may include an integrated or peripheral specialized mathematics keyboard 611 to facilitate the inputting of special and non-standard mathematical symbols. Additionally, specialized display screens 612 and other outputs may be used in some cases to render and display special and non-standard mathematical symbols and expressions. In certain embodiments, expression input devices 610 cases may include combinations of specialized software and hardware components used for inputting and outputting mathematical expressions. For example, a touchscreen display and/or stylus pen may be combined with software functionality used to identify and distinguish mathematical symbols and combinations of symbols in expressions. In other cases, sequences and/or combinations of keys may be depressed on a standard keyboard 411 or touchscreen keyboard, such that each unique key sequence or combination may represent a different mathematical symbol. A specialized software-based math input display panel also may be rendered on a display screen 612, and the user may identify and select a desired symbol using a mouse, keyboard, or touchscreen capability, etc. In still other cases, microphones and/or cameras may be used along with voice or gesture recognition and control software to allow users to input mathematical symbols and expressions via an expression input device 610.

Mathematical expression conversion systems 600 also may include various display devices configured to output data corresponding to mathematical expressions, including one or more refreshable braille display devices 630 and one or more visual display devices 640. In some embodiments, expression input devices 610 may be similar or identical to display devices 630 and/or 640, in that such devices may include both input components for receiving mathematical expression input data and output components for displaying mathematical expression output data. In fact, designated expression input devices 610 may be optional in some systems 600, and one or more of the display devices 630 and/or 640 may be used for inputting and outputting mathematical expression data. Additionally, although these examples include both refreshable braille display devices 630 and visual display devices 640, other examples may include either a set of refreshable braille display devices 630 or a set of visual display devices 640, but not both. As discussed below, expression converters and/or conversion processes may be used even in cases when only one type of display device (e.g., 630 or 640) is used within the system 600.

Refreshable braille display devices 630 may include one or more electromechanical braille cells configured to display braille characters for braille readers. In some cases, a plurality of electromechanical braille cells may each include a plurality of output dots (e.g., round-tipped pins) which may be raised and lowered based on the voltages applied to the electromechanical braille cell. Different combinations of output dots may be raised and lowered to represent different characters. As discussed below, certain common mathematical symbols such as letters, numbers, and arithmetic operators may be represented using a single braille cell, while multiple braille cells may be required to represent other mathematical symbols such as special and non-standard symbols. Illustrative examples of refreshable braille display devices 630 may include, without limitation, the BRAILLE SENSE U2 NOTETAKER by HIMS INC., or the BRAILLIANT BRAILLE DISPLAY by HUMANWARE, among others.

In addition to the panels of electromechanical braille cells 632, certain braille display devices 630 may include a keypad 631 for entry of mathematical symbols and expressions. In some cases, keypads 631 may correspond to a standard keyboard, optionally including braille dots affixed to some or all of the individual keys to aid visually impaired users. In other cases, keypads 631 may include specialized braille keyboards (e.g., Perkins style, 6-key or 8-key chorded keyboards used for braille typing). Additionally, in some embodiments, one or more braille display devices 630 may include additional hardware and software for receiving mathematical expression input and displaying mathematical expression output for visually impaired users, such as microphones and voice recognition and control functionality for receiving/processing mathematical symbols and expressions, and device speakers and speech synthesizers for outputting mathematical symbols and expressions.

Visual display devices 640 may include any computing devices configured to receive and display mathematical expression output. As previously noted, visual display devices 640 may be similar or identical to the expression input devices 610, and thus may include desktop and laptop computers, smartphones, tablet computers, mobile devices, and any other computing device capable of displaying mathematical symbols and expressions. As shown in this example, certain visual display devices 640 may include one or more input components 641 and/or output components 642, which may include peripheral devices or I/O components integrated within the device. For example, output components 642 may correspond to display screens for displaying mathematical expressions. In some cases, visual display devices 640 may include standard computer display screens 642, while in other cases the display screens 642 may be specialized for rendering and displaying mathematical symbols and expressions. For instance, displaying of certain mathematical symbols and expressions may require (or may preferably include) display capabilities such as a minimum screen size, minimum display resolution, color display, graphics or video capabilities, 3D display capabilities, and the like. Additionally, visual display devices 640 including such specialized display screens 642 may include corresponding specialized software components and underlying hardware for rendering and outputting to the display screen 642, such as specialized graphics components (e.g., graphics processors, graphics drivers, 3D graphics support, etc.), mathematical symbol libraries, mathematical expression rendering software packages, and the like.

In shown in this example, expression converter 620 may communicate with expression input devices 610 and one or more braille display devices 630 and/or visual display devices 640 via communication networks 220. As shown in this example, an expression converter 620 may be implemented as a server, device, or other standalone hardware and software system within a mathematical expression conversion system 600. In other examples, an expression converter 620 may be integrated within one or more servers or other components of an associated CDN 100. For example, an expression converter 620 may be implemented as specialized software within a content management server 102 or other CDN component, and may leverage much of the existing hardware and software infrastructure of the CDN 100 to convert mathematical expressions for devices 610, 630, and 640 (which may correspond to user devices 106 and supervisor devices 110, etc.) within an educational or professional training CDN 100, a mathematical presentation and collaboration CDN 100, an interactive math-based gaming CDN 100, etc.

Expression converter 620 may include multiple different converters and/or conversion processes for performing the various mathematical expression conversions described herein. For example, expression converter 620 may include one or more of a math input-to-content markup converter 621, a content markup-to-braille converter 622, a content markup-to-presentation markup converter 623, and a braille-to-content markup converter 624. The functionality of converters 621-624 is described below in reference to FIGS. 7-9. In various embodiments, converters 621-624 may be implemented as separate converters using dedicated hardware resources and/or executable software components. Alternatively or additionally, some or all of the converters 621-624 may be combined to use the same software executable and/or underlying hardware resources. In any such embodiments, each converter 621-624 may maintain and apply a specific set of mathematical expression conversion rules that is unique to the individual converter 621-624 and/or conversion processes applied. As discussed below in more detail, these expression conversion rules may include character mapping rules as well as special encoding and decoding rules used specifically for mathematical expressions that do not correspond to character mapping rules. Different sets of special encoding and decoding rules may be stored and applied by each converter 621-624 and/or conversion process, and may be used to provide uniformity of presentation and to reduce (or even eliminate) ambiguous mathematical expressions during the conversion and braille and/or visual display processes. The various conversion rules for mathematical expressions used by converters 621-624 may be stored within the memory of the converters 621-624 themselves, or within an external data store 625. In some embodiments, storing some or all such conversion rule within an external data store 625 may allow for the rules to be updated dynamically and seamlessly without affecting the execution of the converters 621-624.

Additionally, in some embodiments, the expression converter 620 might not be implemented separately from the expression input devices 610, refreshable braille display devices 630, and/or visual display devices 640, but instead may be implemented within these devices leveraging the various hardware and software components therein. Thus, implementing the expression converter 620 as a separate server or device as shown in FIG. 6, and/or within any CDN server-side component (e.g., CMS 102, content server 112, administrative server 116, etc.) may be optional in such embodiments. Instead, each of the expression input devices 610, refreshable braille display devices 630, and/or visual display devices 640 may include one or more of the converter components 621-624. For instance, refreshable braille display devices 430 may include a content markup-to-braille converter 622 and a braille-to-content markup converter 624. Similarly, expression input devices 610 and/or visual display devices 440 may include a math input-to-content markup converter 621, and a content markup-to-presentation markup converter 623. For visual display devices 440 that support braille display capabilities (see, e.g., FIG. 12-14), such visual display devices 440 may also include braille converters 622 and 624.

Figure 7:
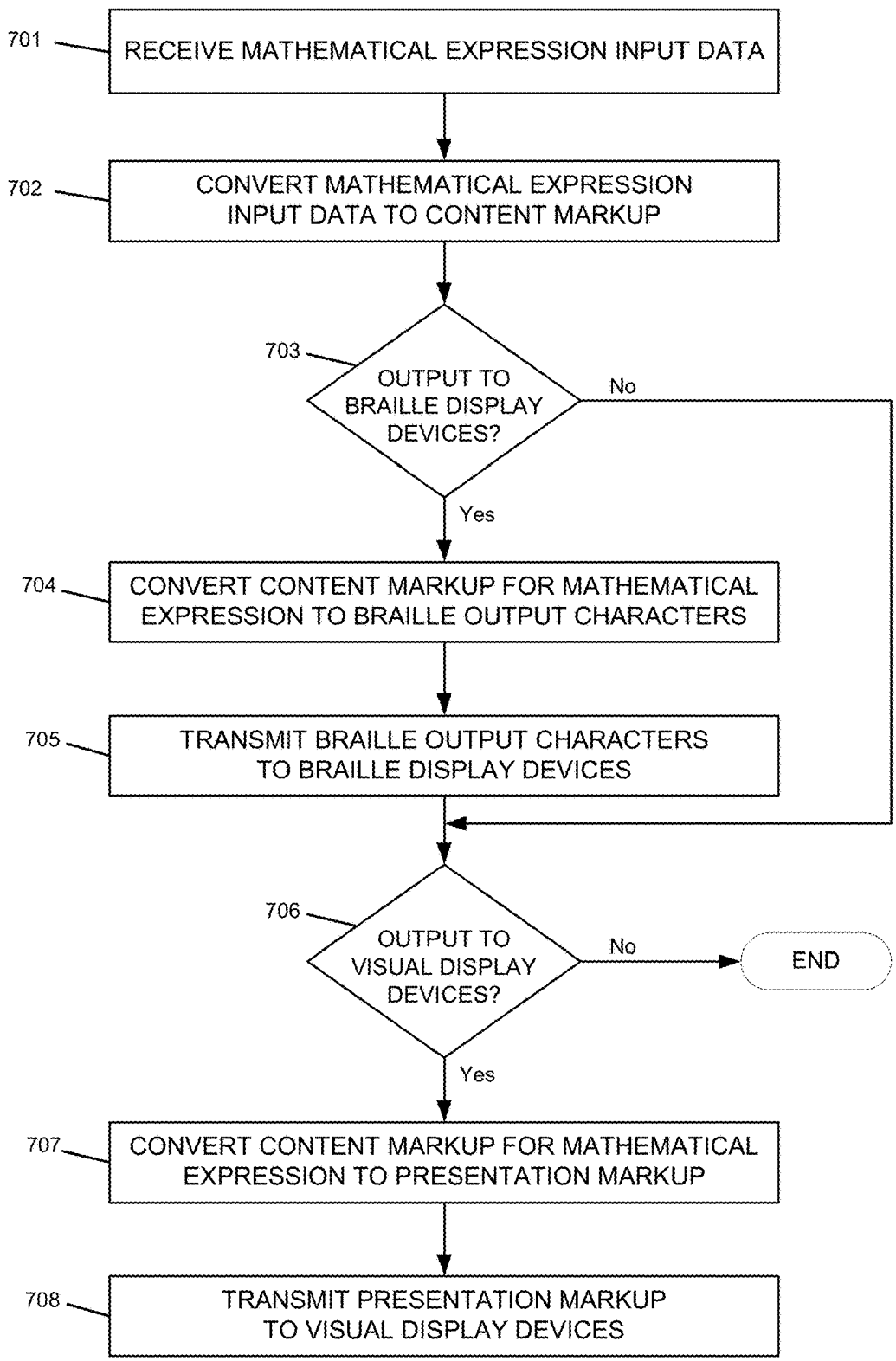
FIG. 7 is a flow diagram illustrating an example process of converting mathematical expression data received from an input device to braille output and/or visual display output, according to one or more embodiments of the disclosure.

Referring now to FIG. 7, a flow diagram is shown illustrating a process of converting mathematical expression data received from an input device to braille output and/or visual display output. As described below, the steps in this process may be performed by one or more components in the mathematical expression conversion systems 600 described above, such as an expression converter 620 and/or various input and output devices 610, 630, and 640. However, it should be understood that the various features and processes described herein, including receiving input data corresponding to mathematical expressions, performing conversion processes on the mathematical expression input data, determining output devices, and transmitting braille output and/or visual output to the appropriate output devices need not be limited to the specific systems and hardware implementations described above in FIGS. 1-6.

In step 701, mathematical expression input data is received, for example, by an expression converter 620 within a mathematical expression conversion system 600. As discussed above, in various different embodiments, expression converters 620 may be implemented as stand-alone servers or devices, integrated within the existing server infrastructure of a CDN 100, and/or integrated within individual user devices such as the expression input devices 610, refreshable braille display devices 630, and/or visual display devices 640 discussed above.

The mathematical expression input data received in step 701 may consist of a single character corresponding to any mathematical symbol (e.g., a number, variable, operator, functions, grouping symbol, etc.) or may comprise an expression having multiple symbols. In some cases, the mathematical expression input data received in step 701 may be received in response to a user input of one or more characters via an expression input device 610 or other user devices 630 and 640 with input capabilities. For example, within an implementation of an educational or professional training software system 600, an interactive gaming system 600, an online presentation system 600, a collaborative work environment 600, etc., a first user (e.g., a presenter, teacher, trainer, etc.) may input one or more mathematical symbols into a mathematical user interface provided on an expression input device 610. In response, the expression input device 610 may transmit data to the expression converter 620 identifying the input characters/symbols. As discussed below, this action by the first user (e.g., inputting or updating a single character of a mathematical expression) may trigger the conversions of the input data and the outputting of the converted mathematical expressions to visual display devices 640 and/or refreshable braille display devices 630, which may be performed in real-time or near real-time in response to the mathematical expression input data received in step 701.

In other cases, the mathematical expression input data received in step 701 need not be received from an expression input device 610 or other user device, but may correspond to data received over a communication network 220. For example, in some embodiments, the receipt of the mathematical expression input data in step 701 may correspond to the expression converter 620 retrieving a web page or other document containing one or more mathematical expressions from a remote server. Such documents may correspond to any type of content resource that may be retrieved and consumed within a CDN 100, such as media content, presentations, educational or professional training content, interactive gaming content, web-based content, any of which may be stored by a content server 112 and/or provided by a content management server 102. In these examples, a server or client system within the CDN 100 may determine that the requested/retrieved content resources include one or more mathematical expressions, and in response may invoke an expression converter 620 implemented within a server (e.g., CMS 102 and/or content server 112), or within a client device such as user devices 106 and/or 110 which may correspond to visual display devices 640 and/or refreshable braille display devices 630, in order to convert and the output the mathematical expression data to the appropriate user devices.

In step 702, the expression converter 620 may execute one or more conversion processes on the mathematical expression input data received in step 701 to convert the mathematical expression to content markup. As used herein, content markup for a mathematical expression may refer to a language or code defining a specified formatting, style, and/or layout for representing mathematical expressions based on the underlying structure of the expression. Thus, content markup is encoded explicitly based on the mathematical structure of the expression, rather than based on any particular visual or oral rendering or representation of the expression. Content markup may be implemented by directly encoding the expression tree structure of the mathematical expression, without any dependency on an additional processing or special parsing of the expression. Thus, a content markup representation of a mathematical expression may be entirely non-ambiguous, unlike certain textual or visual representations of mathematical expression that may be ambiguous in some cases. Examples of different content markup definitions that may be used in step 702 include any of content markup specifications within the Mathematical Markup Language (MathML) editions and/or versions defined by the World Wide Web Consortium (W3C), although it should be understood that these examples are illustrative only and non-limiting, and that other content markup definitions or specifications may be used in other examples.

In some embodiments, the conversion process performed in step 702 may include a conversion from ASCII, Unicode (e.g., UTF-8 or UTF-16), or another visual display format, to content markup. To perform the conversion in step 702, the expression converter 620 may invoke the math-to-content markup converter 621 and/or the applicable expression conversion rules for math-to-content markup conversion from an expression conversion rules data store 625. Converter 621 may be configured to parse the mathematical expression input, identify the structural components of the expression (e.g., determine an expression tree corresponding to the input), and then generate and populate the corresponding markup elements. Additional conversions that may be performed in step 702 may include an initial handwriting to ASCII or Unicode conversion, voice-to-text conversion, etc., which may be used when the mathematical expression input data received in step 701 corresponds to handwriting or voice data, and so on. Referring briefly to FIGS. 10A and 11A, two examples of content markup are shown that may be generated in step 702, based on received input corresponding to the textual mathematical expression shown above each text box in these examples.

In step 703, the expression converter 620 may determine whether or not any refreshable braille display devices 630 are present in the system 600 to receive the mathematical expression output. For example, the mathematical expression input in step 701 may be received during an interactive computing session within a CDN 100, such as an online presentation, eLearning lecture or interactive learning session, interactive gaming session, or collaborative remote work session. In any of these examples, the expression input device 610 may correspond to a user device 106 or 110 of a participant, presenter, collaborator, etc. The expression converter 620 may determine in step 703 whether any of the other user devices participating in the online presentation session, eLearning lecture or interactive learning session, interactive gaming session, or collaborative remote work session, are refreshable braille display devices 630. If a system 600 includes one or more currently active refreshable braille display devices 630 (703:Yes), then the expression converter 620 may determine that braille output should be generated and output to these devices 630. For example, if a set of user devices 106 receiving a live presentation, participating in a real-time collaborative work session, or receiving other CDN content resources, includes one or more of the braille display devices 630*a*-630*c* (703:Yes), then the expression converter 620 may convert the mathematical expression to braille output as described below in step 704. However, if no braille readers are using refreshable braille display devices 630 to receive and participate in the communication session (703:No), then the expression converter 620 may determine not to generate braille output. For example, if the set of user devices 106 receiving a live presentation, participating in a real-time collaborative work session, or receiving other CDN content resources, includes only visual display devices 640*a*-640*c* and no braille display devices 630 (703:No), then the expression converter 620 may determine that there is no need to convert the receive mathematical expression input data into braille output in step 704.

In some embodiments, step 703 may be optional, and the expression converter 620 may determine that braille output should be generated in all cases. Thus, in such embodiments, the expression converter 620 need not be aware of which user devices 106 (if any) are receiving, participating in the session, or otherwise consuming the content resources including the mathematical expression input received in step 701, but instead may simply perform all conversion processes described herein in response to each received mathematical expression input.

In step 704, the expression converter 620 may execute one or more conversion processes on the content markup data generated in step 702 to convert the content markup to braille output characters. To perform the conversion in step 704, the expression converter 620 may invoke the content markup-to-braille converter 622 and/or the applicable expression conversion rules for content markup-to-braille conversion from an expression conversion rules data store 625. The output generated by the content markup-to-braille converter 622 in step 704 may correspond to Nemeth Braille Code for Mathematics, and/or any other braille mathematical notation. Converter 622 may be configured to parse content markup generated in step 702, and identify the proper braille characters and the appropriate format and presentation order for the braille characters to be displayed. The conversion rules integrated within and/or applied by the content markup-to-braille converter 622 may include one-to-one character mapping rules (i.e., rules mapping a single mathematical symbol to a single braille symbol), one-to-many character mapping rules (i.e., rules mapping a single mathematical symbol to multiple braille symbols), and/or various special braille encoding rules for mathematical expressions that do not correspond to one-to-one or one-to-many character mapping rules. Such special braille encoding rules, discussed below in more detail in reference to FIGS. 12-14, may be used to provide uniformity of presentation of braille output and to reduce or eliminate ambiguity for the represented mathematical expression.

In step 705, the expression converter 620 may transmit the braille output characters (also referred to as braille symbols) to the appropriate refreshable braille display devices 630. As noted above, the recipient devices 630 in step 705 may correspond to the set of braille display devices 630 participating in an online presentation session, eLearning lecture or interactive learning session, interactive gaming session, or collaborative remote work session, etc. Accordingly, the braille conversion in step 704 and transmission in step 705 may be performed in real-time or near real-time with respect to the mathematical expression input received in step 701, so that refreshable braille display devices 630 may receive and output the converted braille characters in real-time or near real-time with respect to the presentation, collaborative work session, etc.

In step 706, the expression converter 620 may determine whether or not any visual display devices 640 are present in the system 600 to receive the mathematical expression output. Thus, step 706 may be performed similarly to step 703. For example, the expression converter 620 may determine in step 706 whether any user devices 106 participating in an online presentation session, eLearning lecture or interactive learning session, interactive gaming session, or collaborative remote work session, are visual display devices 640. If a system 600 includes one or more currently active visual display devices 640 (706:Yes), then the expression converter 620 may determine that visual mathematical expression output (e.g., presentation markup) should be generated and output to these devices 640. However, if no visual display devices 640 are currently receiving and/or participating in the communication session (706:No), then the expression converter 620 may determine not to generate presentation markup as output. Additionally, as described above for step 703, step 706 also may be optional in some embodiments, and the expression converter 620 may determine that visual output (e.g., presentation markup) should be generated in all cases. Thus, in such embodiments, the expression converter 620 need not be aware of which user devices 106 (if any) are receiving, participating in the session, or otherwise consuming the content resources including the mathematical expression input received in step 701.

In step 707, the expression converter 620 may execute one or more conversion processes on the content markup data generated in step 702 to convert the content markup to presentation markup. To perform the conversion in step 707, the expression converter 620 may invoke the content markup-to-presentation markup converter 623 and/or the applicable expression conversion rules for content markup-to-presentation markup conversion from an expression conversion rules data store 625. In contrast to the content markup, the presentation markup for a mathematical expression may define a specified formatting, style, and/or layout for representing mathematical expressions based on the visual rendering and displaying of the expressions on a display screen. Thus, presentation markup may be structured using elements such as rows, characters/symbols within rows, superscript and subscript designations, square root symbols, and other similar elements which define the visual rendering of the expression, rather than elements corresponding to the expression tree structure of the mathematical expression. Examples of different presentation markup definitions that may be used in step 707 include any of presentation markup specifications within the Mathematical Markup Language (MathML) editions and/or versions defined by the World Wide Web Consortium (W3C), although it should be understood that these examples are illustrative only and non-limiting, and that other presentation markup definitions or specifications may be used in other examples. For instance, referring briefly to FIGS. 10B and 11B, two specific examples of presentation markup are shown that may be generated in step 707, based on content markup. The presentation markup shown in these examples may correspond to the content markup shown in FIGS. 10A and 11A, respectively, and to the mathematical expressions shown above each text box in these examples.

In step 708, the expression converter 620 may transmit the presentation markup output to the appropriate visual display devices 640. As noted above, the recipient devices 640 in step 708 may correspond to the set of visual display devices 640 participating in an online presentation session, eLearning lecture or interactive learning session, interactive gaming session, or collaborative remote work session, etc. Accordingly, the conversion to presentation markup in step 707 and transmission in step 708 may be performed in real-time or near real-time with respect to the mathematical expression input received in step 701, so that visual display devices 640 may receive and output the converted presentation markup in real-time or near real-time with respect to the presentation, collaborative work session, etc.

Figure 8:
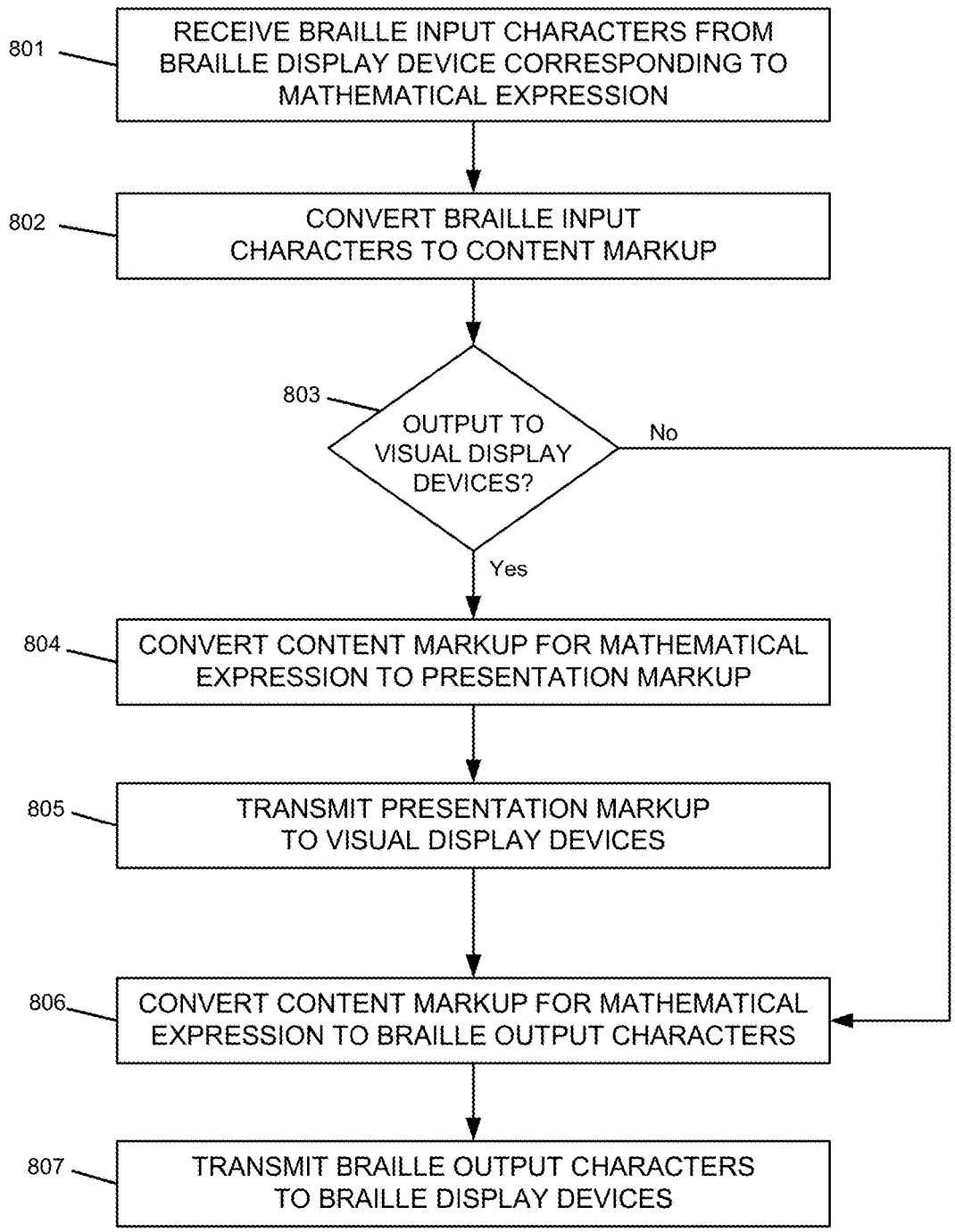
FIG. 8 is a flow diagram illustrating an example process of converting mathematical expression input data received from a braille device to braille output and/or visual display output, according to one or more embodiments of the disclosure.

Referring now to FIG. 8, a flow diagram is shown illustrating a process of converting mathematical expression data received from a braille input device to braille output and/or visual display output. In some embodiments, the steps described in connection with FIG. 8 may be similar or identical to the steps described in FIG. 7. However, in contrast to the FIG. 7, the example described in FIG. 8 specifically describes scenarios in which the mathematical expression input received includes braille input characters received from a braille input device 430. As with FIG. 7, discussed above, the steps in this process may be performed by components in the mathematical expression conversion systems 600 described above, such as an expression converter 620 and/or various input and output devices 610, 630, and 640, although the various features and processes described herein need not be limited to the specific systems and hardware implementations described above in FIGS. 1-6.

In step 801, mathematical expression input data is received, for example, by an expression converter 620. In this example, the input data corresponds to one or more braille characters received from a braille input device. As discussed above, certain refreshable braille display devices 430 may also be braille input devices, and such devices 430 may include braille keyboards and/or other specialized components for receiving mathematical expression input from visually impaired users. In other cases, braille input devices need not include refreshable braille displays.

In some embodiments, step 801 may be similar or identical to step 701, and any of the mathematical symbols and mathematical expressions discussed above in reference to stop 701 may similarly be received in step 801. For instance, if the expression input device 610 discussed above is a braille input device 610, then the mathematical expression input data received in step 701 may correspond to braille input characters, but all other steps discussed above in FIG. 7 may be performed similarly or identically. In other cases, the braille input received in step 801 may correspond to a response or editing of the initial mathematical expression input by a different user in step 701. For example, the steps described in FIG. 7 may correspond to a process in which a first user (e.g., a presenter, teacher, trainer, co-worker, etc.) inputs a mathematical expression into a first device 610 within an implementation of an educational or professional training software system 600, an interactive gaming system 600, an online presentation system 600, a collaborative work environment 600, or the like, and the mathematical expression input is then converted and transmitted to one or more additional display devices 630 and/or 640. Continuing this example, after the steps described in FIG. 7 are performed, the steps described in FIG. 8 may be performed, corresponding to a process in which a different user responds to the initial communication of the first user by altering or editing the initial mathematical expression (e.g., correcting the work of the first user, making a suggestion of a different mathematical expression, etc.), or by providing a different responsive mathematical expression (e.g., answering a math question contained in the initial communication), using a braille input device (e.g., 430).

In step 802, the expression converter 620 may execute one or more conversion processes on the braille input characters received in step 801 to convert the mathematical expression to content markup. To perform the conversion in step 802, the expression converter 620 may invoke the braille-to-content markup converter 624 and/or the applicable expression conversion rules for braille-to-content markup conversion from an expression conversion rules data store 625. In some embodiments, the braille-to-content markup conversion may be similar to the math-to-content markup conversion described above in step 701, although braille characters may be used as the initial input to the conversion process rather than ASCII or Unicode characters. Additionally, in some embodiments, the braille-to-content markup conversion process may be similar but converse to the content markup-to-braille conversion described above in 704. However, as noted above, each of the separate converters 621-624 and/or conversion processes described herein may use separate and unique conversion rules, including character mapping rules (e.g., one-to-one, one-to-many, and many-to-one character mappings) as well as special encoding and decoding rules for mathematical expressions that do not correspond to character mappings.

In step 803, the expression converter 620 may determine whether or not any visual display devices 640 should receive the mathematical expression output. Thus, step 803 may be similar or identical to step 706, discussed above. For example, the expression converter 620 may determine in step 803 whether any user devices 106 participating in an online presentation session, eLearning lecture or interactive learning session, interactive gaming session, or collaborative remote work session, are visual display devices 640. If a system 600 includes one or more currently active visual display devices 640 (803:Yes), then the expression converter 620 may determine that visual mathematical expression output (e.g., presentation markup) should be generated and output to these devices 640. In such cases, in step 804, the expression converter 620 may execute one or more conversion processes on the content markup data generated in step 802 to convert the content markup to presentation markup. Then, in step 805, the expression converter 620 may transmit the presentation markup output to the appropriate visual display devices 640. Steps 804 and 805 may be similar or identical to steps 707 and 708, discussed above.

In step 806, the expression converter 620 may execute one or more conversion processes on the content markup data generated in step 802 to convert the content markup to braille output characters. Then, in step 807, the expression converter 620 may transmit the braille output characters to the appropriate refreshable braille display devices 630. Thus, steps 806 and 807 may be similar or identical to steps 704 and 705, discussed above.

It should be noted that the conversions described in this example include a first conversion from braille input characters to content markup in step 802, and a second conversion from the content markup back to braille output characters in step 806. Performing both of these conversions may be advantageous in some cases, for example, if the mathematical expression input received from the user device in step 801 is potentially mathematically ambiguous, or if it is expressed in a non-standard and/or non-uniform way. For instance, if the user inputs a mathematical expression such as "a+b" or "a(b)" it may be unclear whether the expression represents a number or a function. Similarly, a user may input any number of potentially ambiguous mathematical expressions, such as "sin xy", "sin ^2 x", "a/2n", or various other ambiguous expressions that have multiple possible intended meanings. By converting the braille input characters first to content markup in step 802, and then back to braille output characters in step 806, any potential ambiguity within the expression may be resolved during the conversion to content markup in step 802, and the braille output representation of the mathematical expression transmitted in step 807 will thus be identical for all braille display devices 430a-430c. By resolving the potential ambiguities in the mathematical expression during the conversion processes, and by providing for uniformity in braille output display, situations may result in which the braille input characters received from a braille device 430a in step 801 do not precisely match the braille output characters transmitted back to the same braille device 430a in step 807.

Moreover, it may be assumed in this example that the braille input device from which the mathematical expression input was received in step 801 will also be a refreshable braille display device on which the mathematical expression should be displayed in step 807. Accordingly, this example process does not include a step corresponding to step 703, in which the expression converter 620 determines whether there are any refreshable braille display devices 630 that should receive the braille output characters.

Figure 9:
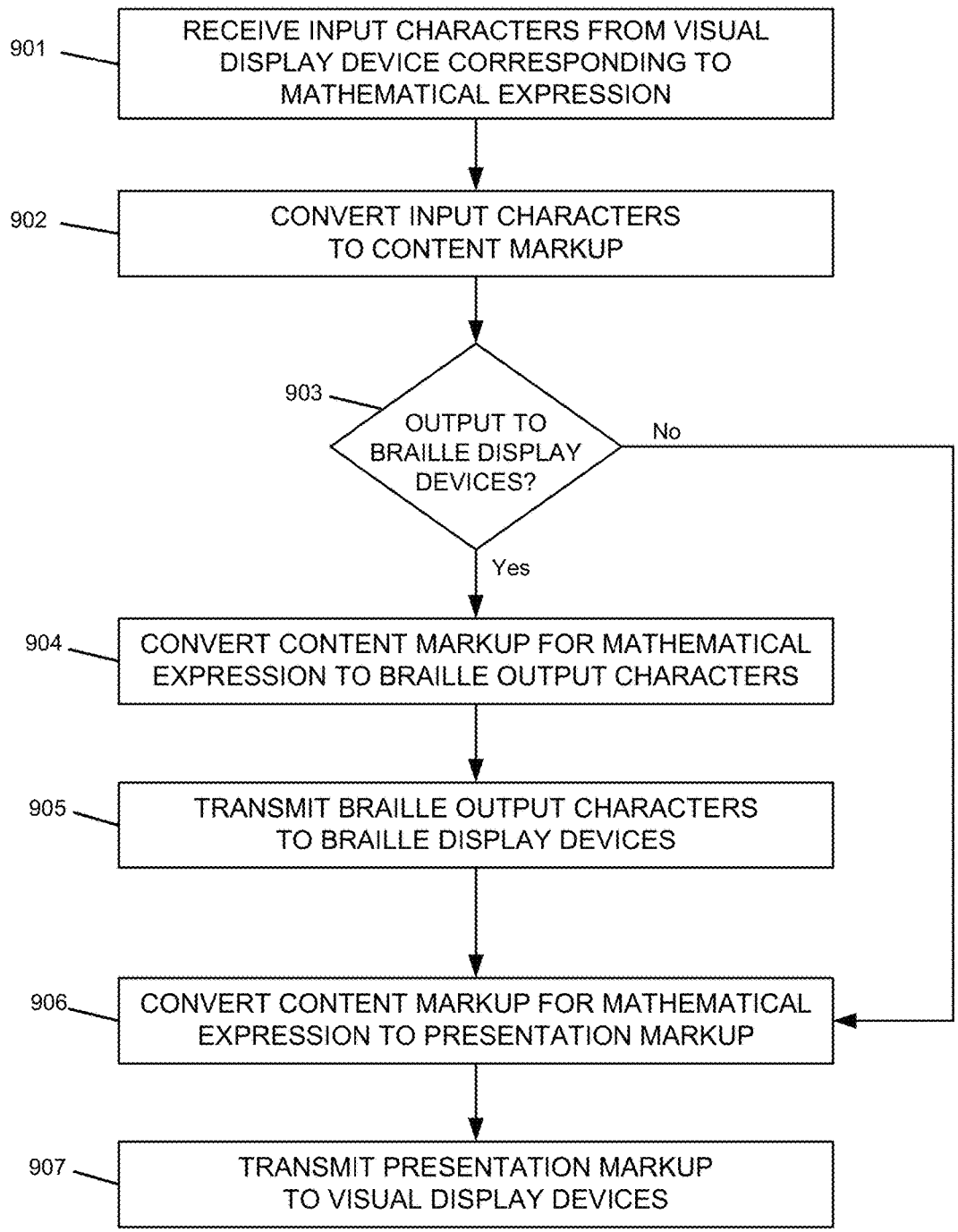
FIG. 9 is a flow diagram illustrating an example process of converting mathematical expression input data received from a visual display device to braille output and/or visual display output, according to one or more embodiments of the disclosure.

Referring now to FIG. 9, a flow diagram is shown illustrating a process of converting mathematical expression data received from a visual display device to visual display output and/or braille output. The steps described in connection with FIG. 8 may be similar or identical to the steps described in FIGS. 7-8. In contrast to the FIG. 8, the example described in FIG. 9 specifically describes scenarios in which the mathematical expression input received includes non-braille input characters received from the input components of a visual display device 440, such as a keyboard, mouse, touchscreen, and/or specialized mathematics software. As with FIGS. 7-8, discussed above, the steps in this process may be performed by components in the mathematical expression conversion systems 600 described above, such as an expression converter 620 and/or various input and output devices 610, 630, and 640, although the various features and processes described herein need not be limited to the specific systems and hardware implementations described above in FIGS. 1-6.

In step 901, mathematical expression input data is received, for example, by an expression converter 620. In this example, the input data corresponds to one or more non-braille mathematical symbols (or characters) received from the inputs of a visual display device 640. Step 901 may be similar or identical to step 701, and any of the mathematical symbols and mathematical expressions discussed above in reference to stop 701 may similarly be received in step 901. In some cases, the steps described in FIG. 7 may correspond to a process in which a first user (e.g., a presenter, teacher, trainer, co-worker, etc.) inputs a mathematical expression into a first device 610 within an implementation of an educational or professional training software system 600, an interactive gaming system 600, an online presentation system 600, a collaborative work environment 600, or the like, and the mathematical expression input is then converted and transmitted to one or more additional display devices 630 and/or 640. Continuing this example, after the steps described in FIG. 7 are performed, the steps described in FIG. 9 may be performed, corresponding to a process in which a different user responds to the initial communication of the first user by altering or editing the initial mathematical expression (e.g., correcting the work of the first user, making a suggestion of a different mathematical expression, etc.), or by providing a different responsive mathematical expression (e.g., answering a math question contained in the initial communication), using a visual display device 440.

In step 902, the expression converter 620 may execute one or more conversion processes on the mathematical input characters received in step 901 to convert the mathematical expression to content markup. The conversion processes used in step 902 may be similar or identical to the conversion processes used in step 702, discussed above, the expression converter 620 may invoke the same math-to-content markup converter 621 and/or the same applicable expression conversion rules for math-to-content markup conversion from an expression conversion rules data store 625.

In step 903, the expression converter 620 may determine whether or not any refreshable braille display devices 630 should receive the mathematical expression output. Thus, step 903 may be similar or identical to step 703, discussed above. For example, the expression converter 620 may determine in step 903 whether any user devices 106 participating in an online presentation session, eLearning lecture or interactive learning session, interactive gaming session, or collaborative remote work session, are braille display devices 630. If a system 600 includes one or more currently active braille display devices 630 (903:Yes), then the expression converter 620 may determine that a braille representation of the mathematical expression should be generated and output to these devices 630. In such cases, in step 904, the expression converter 620 may execute one or more conversion processes on the content markup data generated in step 902 to convert the content markup to braille output characters. Then, in step 905, the expression converter 620 may transmit the braille output characters representing the mathematical expression to the appropriate refreshable braille display devices 630. Steps 904 and 905 may be similar or identical to steps 704 and 705, discussed above.

In step 906, the expression converter 620 may execute one or more conversion processes on the content markup data generated in step 802 to convert the content markup to presentation markup. Then, in step 907, the expression converter 620 may transmit the presentation markup output to the appropriate visual display devices 640. Thus, steps 906 and 907 may be similar or identical to steps 707 and 708, discussed above.

As discussed above for FIG. 8, it should be noted that the conversions described in FIG. 9 include a first conversion from mathematical input characters to content markup in step 902, and a second conversion from the content markup back to visual output (e.g., presentation markup) in step 906. Performing both of these conversions may be advantageous for resolving potential ambiguities within the mathematical expression input data received in step 901, as well providing a standard and uniform set of visual output to all visual display devices 640, as discussed above. Moreover, it may be assumed in this example that the visual input device from which the mathematical expression input was received in step 901 will also be a visual display device on which the mathematical expression should be displayed in step 907. Accordingly, this example process does not include a step corresponding to step 706, in which the expression converter 620 determines whether there are any visual display devices 440 that should receive the presentation markup representing the mathematical expression.

Referring now to FIGS. 12, 13, and 14A-14C, several example user interface screens are shown from a braille conversion application. The braille conversion application shown in these examples may be implemented using an underlying expression converter 620, discussed above, which may be configured to convert braille mathematical expression input to text (e.g., presentation markup) output, as well as text or other visual mathematical expression input to braille output. In these examples, each user interface displays an upper text input/output window 1210 and a lower braille input/output window 1220. When a user inputs mathematical characters into the text window 1210 using the math symbol selection panel 1230, the underlying expression converter 620 may perform one or more of the mathematical expression conversion processes described below in reference to FIGS. 7-9. For example, in response to one or more mathematical characters being input, revised, or deleted from the text window 1210, the expression converter 620 may perform a first conversion of the entire expression within the text window 1210 from mathematical input into content markup, followed by a second conversion of the newly generated content markup into braille output characters for display within the braille window 1220. Similarly, in response to one or more braille characters being input, revised, or deleted from the braille window 1220, the expression converter 620 may perform a first conversion of the entire mathematical expression within the braille window 1220 from braille input characters into content markup, followed by a second conversion of the newly generated content markup into presentation markup for display within the text window 1210. Additionally, it should be understood that the braille input/output window 1220 is displayed visually in these examples in order to better illustrate the conversion processes and the braille encoding and decoding rules implemented by the expression converter 620. However, in other examples, the braille window 1220 may correspond to one or more separate refreshable braille display devices 430, and the text window 1210 may correspond to one or more visual display devices 440.

Figure 12:
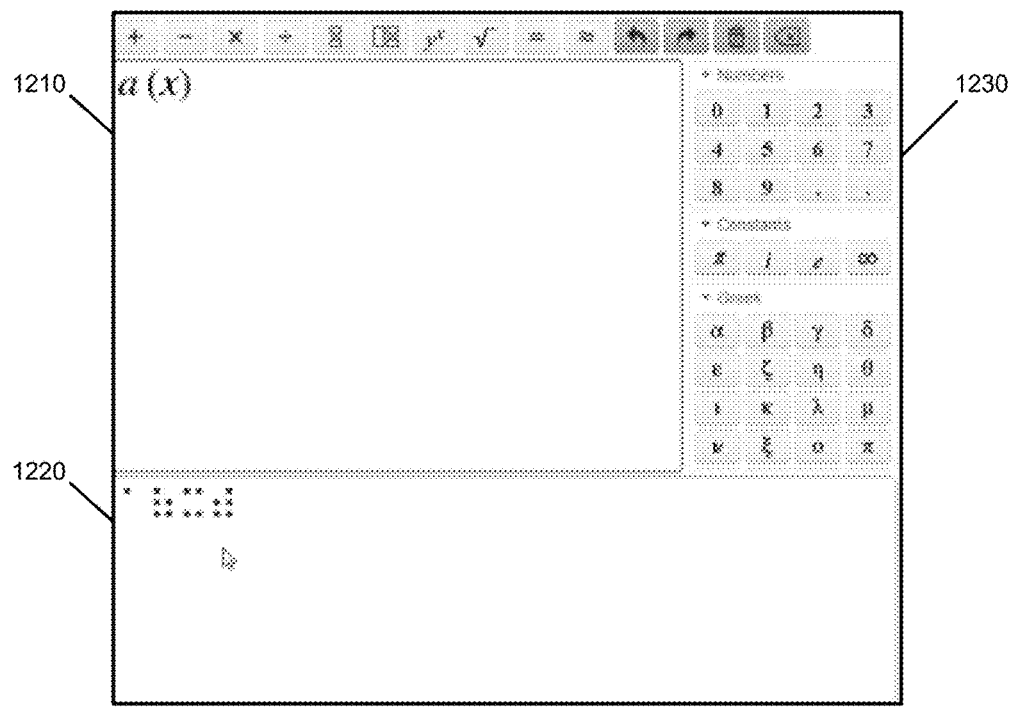
FIGS. 12, 13, and 14A-14C show various examples of visually displayed mathematical expressions along with corresponding braille output, according to one or more embodiments of the disclosure.
Figure 13:
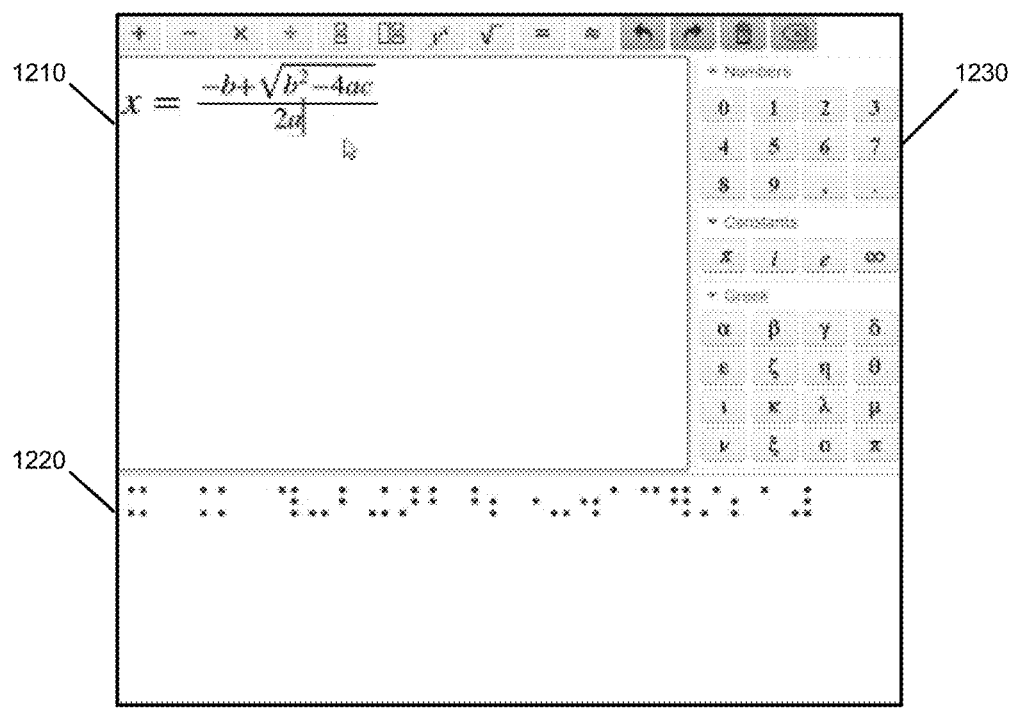

In FIG. 12, the four mathematical characters "a(x)" have been input either into the text window 1210 or the braille window 1220, and the expression converter 620 has performed the conversion processes described above to generate and transmit the corresponding output into the other window. FIG. 13 shows a more complex mathematical expression, but a similar or the same conversion processes may be used by the expression converter 620 to convert from braille input to visual output, or vice versa. In these examples, symmetrical character mapping rules may be applied by the expression converter 620 during the braille-to-content markup and content markup-to-braille conversions. For example, certain mathematical symbols may be mapped to single braille characters by the expression converter 620, while other mathematical symbols may be mapped to combinations of braille characters.

Figure 14A:
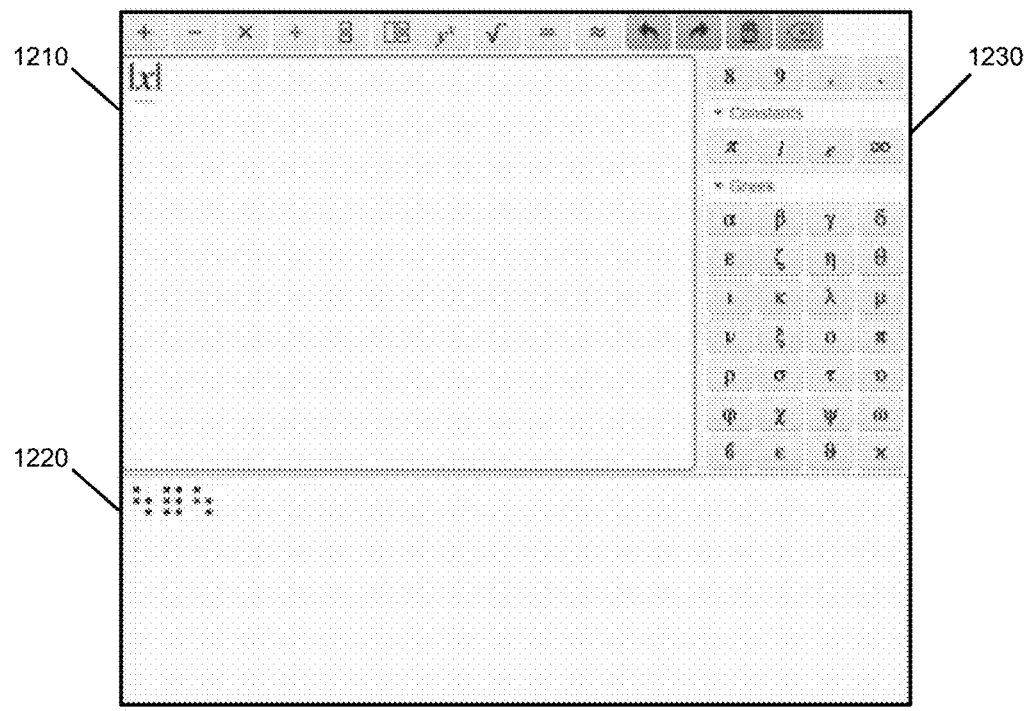
Figure 14B:
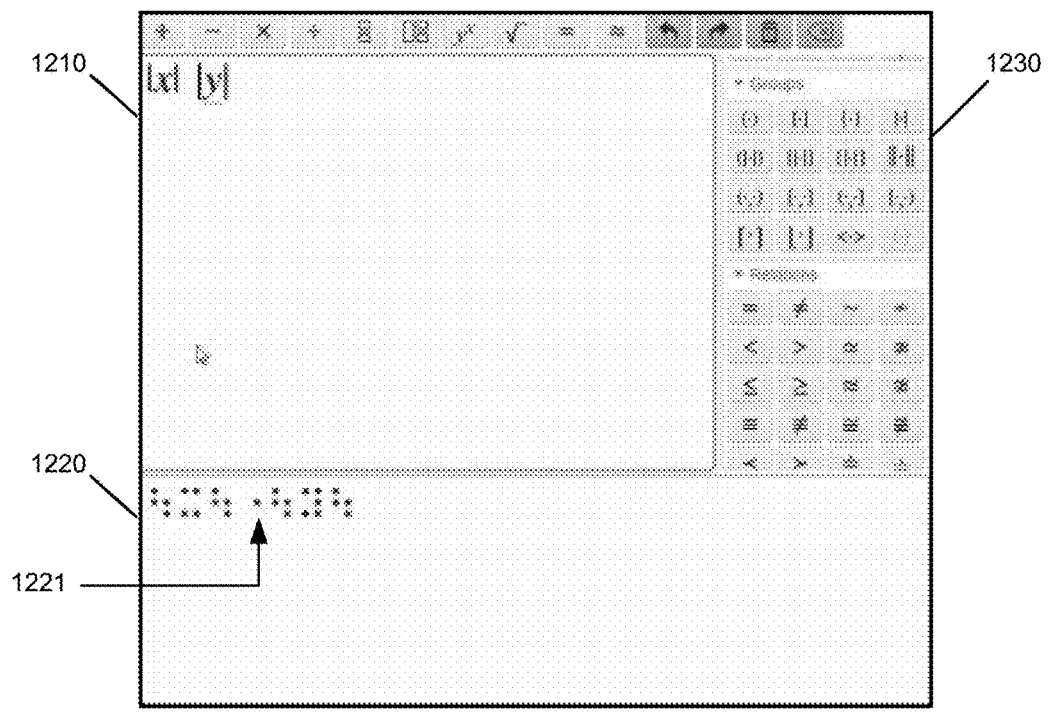
Figure 14C:
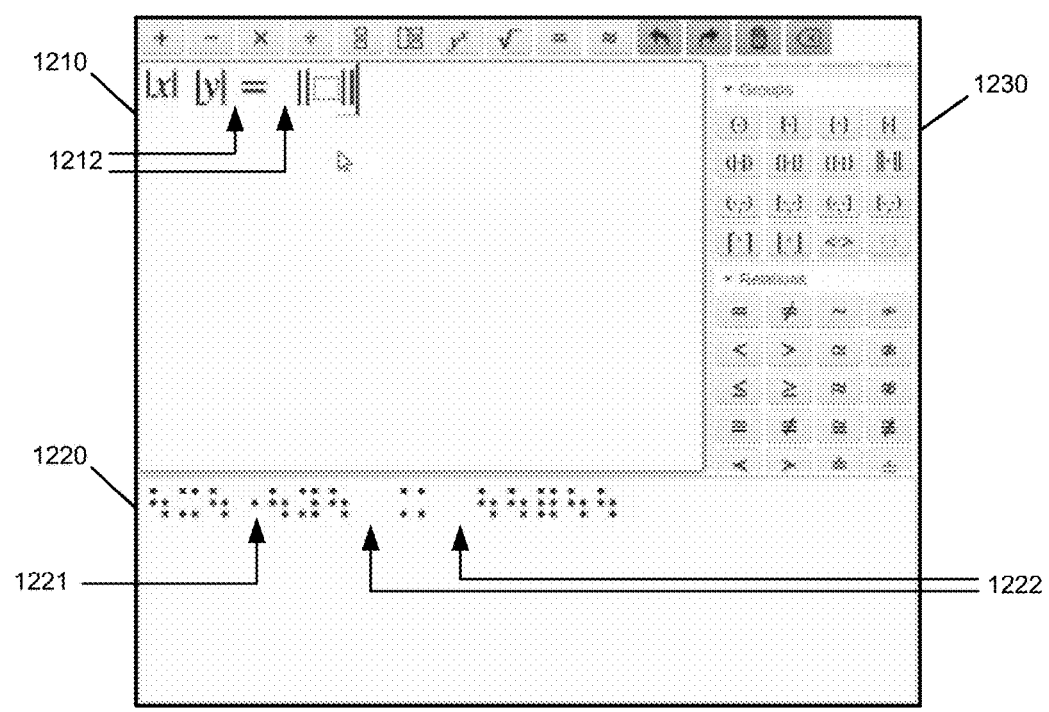

FIGS. 14A-14C show another example in which a user is inputting a sequence of mathematical characters either into the text window 1210 or the braille window 1220, and the expression converter 620 has been invoked at each step to perform the conversion processes described above to generate and transmit the corresponding output into the other window. These figures also illustrate examples of special braille encoding and decoding rules that do not correspond to character mapping rules. Special rules may be designed and applied by the expression converter 620 to avoid ambiguities within the converted mathematical expressions, and to address special braille encoding and decoding situations that may arise. As noted above, each different converter 621-624 and/or conversion process described herein may invoke its own set of special rules for braille encoding and decoding.

In FIG. 14A, an absolute value operation "|x|" is shown in text window 1210, and the three corresponding braille characters (i.e., a first vertical bar braille character (dot-1256), a braille letter "x", and then a second vertical bar braille character (dot-1256)) are shown in the braille window 1220. In FIG. 14B, two consecutive absolute value operations "|x||y|" are shown in text window 1210, and the corresponding braille window 1220 shows the corresponding braille characters for the two consecutive absolute value operations, separated by a multi-purpose indicator 1221. As seen in this example, the multi-purpose indicator 1221 is represented by a single dot braille character (dot-5). The reason for the multi-purpose indicator 1221 is to resolve avoid the potential ambiguity of two consecutive vertical bar braille characters (e.g., (dot-1256) (dot-1256)), which may otherwise indicate a mathematical norm operator "||". It should be understood that this example is illustrative only and non-limiting, and that other multi-purpose indicators 1221 may be inserted during the processes of converting mathematical expressions into braille or from braille, in order to avoid any other potential ambiguities within the braille output or visual output. Additionally, although the multi-purpose indicator 1221 is a single dot braille character (dot-5), it should be understood that other characters or combinations of characters may be used to avoid ambiguities in other examples. In FIG. 14C, additional input has been added to transform the expression in FIG. 14B to an equation "|x||y|=||☐||". This figure again shows the use of the multi-purpose indicator 1221 to distinguish two consecutive absolute value operators from a norm operator. Additionally, in this example, a special spacing rule has been applied by the expression converter 620, in which a space characters 1212 and 1222 have been added to each side of the equal sign in both the visual output and the braille output. The spacing rule in this example may be enforced by the expression converter 620 to avoid ambiguity, increase readability of the braille output characters, and also to provide uniformity between the braille output and the visual output.

Any number of other examples of special braille encoding and/or decoding rules may be implemented in other embodiments. For example, special rules for converting mathematical expressions containing nested fractions into braille and/or from braille may be implemented in some cases. For instance, in some embodiments, an expression converter 620 may convert a simple fraction (i.e., a fraction that does not itself contain a fraction) using a fraction indicator braille character, a fraction bar braille character, and a fraction terminator braille character, while a complex fraction (i.e., a fraction that contains at least one other fraction) may use additional nested fraction indicator braille characters. Thus, the simple fraction ¾ may be encoded into braille as: [fraction indicator character] 3 [fraction bar character] 4 [fraction terminator character], while the complex fraction (⅔)/4 may be encoded into braille as [nested fraction indicator character] [fraction indicator character] 2 [fraction bar character] 3 [fraction terminator character] [nested fraction bar character] 4 [nest fraction terminator character]. For illustrative purposes only, the fraction indicator may be represented by the braille character (dot-1456), and the nested fraction indicator may be represented by the braille character string (dot-6) (dot-1456). To represent each additional enclosed fraction, an additional (dot-6) braille character may be added to the fraction indicator, the fraction bar, and the fraction terminator, in these examples.

A set of special braille encoding and/or decoding rules may be implemented for handling nested roots, similar to rules discussed above for handling nested fractions. For example, additional nested root indicator braille characters may be defined, and an extra braille character (e.g., dot-46) may be added to the open and close root indicators for each enclosed (not enclosing) root. Accordingly, the deeper into a nested root expression, the more dots that will be used to encode the root operator. Additionally, special encoding and/or decoding rules may be used for representing braille subscripts and/or superscripts in some embodiments. For example, the standard braille encodings for superscripts and subscripts may be "x ^i" and "x sub i" respectively. However, in some cases, abbreviated braille encodings may be used for subscripts and/or superscripts when the subscript or superscript is a numeral. Thus, expressions like "x ^2" and "x sub 4" might each be represented by only two braille characters in some cases.

It should be understood that the above examples of special braille encoding rules for mathematical expressions are illustrative only and non-limiting, and that other special braille encoding rules may be implemented in other examples in order to avoid ambiguities within the mathematical expressions, improve readability of the braille output or visual output, or provide uniformity between the braille and visual outputs. Additionally, different sets of encoding and decoding rules may be implemented for conversions between braille input and visual output, and vice versa.

A number of variations and modifications of the disclosed embodiments can also be used. Specific details are given in the above description to provide a thorough understanding of the embodiments. However, it is understood that the embodiments may be practiced without these specific details. For example, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A braille generator and converter system comprising:
one or more refreshable braille display devices, each refreshable braille display device comprising:
  a plurality of electromechanical braille cells, each electromechanical braille cell comprising a plurality of output dots configured to raise and lower in response to voltages applied at the electromechanical braille cell;
  a processing unit comprising one or more processors; and
  memory coupled with and readable by the processing unit and storing therein a set of instructions which, when executed by the processing unit, causes the refreshable braille display device to:
    receive data corresponding to one or more braille output math characters;
    determine an electromechanical braille cell for displaying each of the braille output math characters; and
    transmit control instructions to each of the determined electromechanical braille cells to display the one or more braille output math characters;
an expression input device, comprising:
  an I/O subsystem configured to receive mathematical expression input data via one or more input devices integrated into or connected with the expression input device;
  a processing unit comprising one or more processors; and
  memory coupled with and readable by the processing unit and storing therein a set of instructions which, when executed by the processing unit, causes the expression input device to:
    receive math input data via the I/O subsystem corresponding to a mathematical expression; and
    transmit data representing the mathematical expression to an expression converter; and
the expression converter, the expression converter comprising:
  a processing unit comprising one or more processors; and
  memory coupled with and readable by the processing unit and storing therein a set of instructions which, when executed by the processing unit, causes the expression converter to:
    initiate a multi-user interactive math computing session including at least one of the refreshable braille display devices and at least one visual presentation device;
    receive the math input data from the expression input device representing presentation markup representation of a the mathematical expression during the multi-user interactive math computing session;
    convert the math input data representing the presentation markup representation of the mathematical expression to a mathematical markup languge (MathML) representation of the mathematical expression, using a first set of data conversion rules for converting presentation markup of mathematical expressions to MathML;
    convert the MathML representation of the mathematical expression to a set of braille output math characters, using a second set of data conversion rules for converting MathML to braille math output, wherein the set of braille math output characters includes at least one braille mathematical symbol that does not correspond to any character in the received input data or in the MathML representation of the mathematical expression;
    transmit the set of braille output characters to the at least one of the refreshable braille display devices configured to receive braille output within the interactive computing session, wherein the converting and transmitting of the braille math output characters is performed in real-time in response to the receiving the math input data representing the presentation markup representation of the mathematical expression;
    receive a plurality of single-character revisions to the mathematical expression during the multi-user interactive math computing session, including at least a first single-character revision received as braille math input from the at least one refreshable braille display device, and a second single-character revision received as presentation markup math input from the at least one visual presentation device; and
    in response to each of the plurality of single-character revisions to the mathematical expression received during the multi-user interactive math computing session;
    (a) determine an input data type of the received single-character revision to the mathematical expression;
    (b) determine a set of conversion rules for converting the revised mathematical expression to MathML based on the determined input data type;
    (c) convert the revised mathematical expression incorporating the single-character revision into revised MathML of the mathematical expression using the determined set of conversion rules;
    (d) convert the revised MathML of the mathematical expression into one or more output math formats comprising at least one of the braille math output or presentation markup math output; and
    (e) transmit the revised mathematical expression, converted into the one or more output math formats, to one or more output devices including at least one of the visual presentation devices or at least one refreshable braille display devices.

2. The braille generator and converter system of claim 1, the memory of the expression converter storing therein further instructions which, when executed by the processing unit, causes the expression converter to:
receive a set of braille input characters from a first refreshable braille display device, the set of braille input characters representing an updated mathematical expression;
retrieve a third set of data conversion rules for converting braille input to MathML, and
convert the received braille input characters representing the updated mathematical expression to a MathML representation of the updated mathematical expression, using the third set of data conversion rules.

3. The braille generator and converter system of claim 2, further comprising:
one or more visual presentation devices, each visual presentation device comprising:
a visual display screen configured to render representations of mathematical expressions;
a processing unit comprising one or more processors; and
memory coupled with and readable by the processing unit and storing therein a set of instructions which, when executed by the processing unit, causes the visual presentation device to:
receive data corresponding to presentation markup representations of mathematical expressions;
parse the received presentation markup representations of the mathematical expressions; and
render mathematical expressions corresponding to the received presentation markup representations on the visual display screen.

4. The braille generator and converter system of claim 3, wherein receiving the input data by the expression input device comprises receiving input of a first set of characters via the I/O subsystem of the expression input device, and
wherein the presentation markup representation of the mathematical expression converted by the expression converter corresponds to a rendering of the mathematical expression including a second set of characters different from the first set of characters.

5. The braille generator and converter system of claim 1, wherein the converting and transmitting of the braille output math characters to the at least one of the refreshable braille display devices is performed simultaneously with converting and transmitting of the presentation markup representation to the at least one visual presentation device.

6. The braille generator and converter system of claim 1, the memory of the expression converter storing therein further instructions which, when executed by the processing unit, causes the expression converter to:
receive, from a first visual presentation device, first additional input data comprising a revision to the mathematical expression made via the first visual presentation device;
receive, from a first refreshable braille display device, second additional input comprising a revision to the mathematical expression made in braille via the first refreshable braille display device, wherein the revision to the mathematical expression made via the first visual presentation device is made simultaneously to the revision to the mathematical expression made via the first refreshable braille display device;
determine an updated mathematical expression based on both the revision to the mathematical expression made via the first visual presentation device and the revision to the mathematical expression made via the first refreshable braille display device;
convert the data representing the updated mathematical expression to a MathML representation of the updated mathematical expression, using the first set of data conversion rules;
convert the MathML representation of the updated mathematical expression to an updated set of braille output characters, using the second set of data conversion rules;
convert the MathML representation of the updated mathematical expression to an updated presentation markup representation using a third set of data conversion rules;
transmit the updated set of braille output characters to the at least one refreshable braille display device including the first refreshable braille display device; and
transmit the updated presentation markup to at least one visual presentation device including the first visual presentation device.

7. A method, comprising:
initiating, by an expression converter, a multi-user interactive math computing session including at least one refreshable braille display device and at least one visual presentation device;
receiving, by the expression converter, math input data representing a presentation markup representation of a mathematical expression during the multi-user interactive math computing session;
converting, by the expression converter, the math input data representing the presentation markup representation of the mathematical expression to a mathematical markup language (MathML) representation of the mathematical expression, using a first set of data conversion rules for converting presentation markup of mathematical expressions to MathML;
converting, by the expression converter, the MathML representation of the mathematical expression to a set of braille output math characters, using a second set of data conversion rules for converting MathML to braille math output, wherein the set of braille math output characters includes at least one braille mathematical symbol that does not correspond to any character in the received input data or in the MathML representation of the mathematical expression;
transmitting, by the expression converter, the set of braille output characters to the at least one refreshable braille display device, wherein the converting and transmitting of the braille output math characters is performed in real-time in response to the receiving the math input data representing the presentation markup representation of the mathematical expression,
receiving, by the expression convertor, a plurality of single-character revisions to the mathematical expression during the multi-user interactive math computing session, including at least a first single-character revision received as braille math input from the at least one refreshable braille display device, and a second single-character revision received as presentation markup math input from the at least one visual presentation device; and
in response to each of the plurality of single-character revisions to the mathematical expression received during the multi-user interactive math computing session;
(a) determining an input data type of the received single-character revision to the mathematical expression;
(b) determining a set of conversion rules for converting the revised mathematical expression to MathML, based on the determined input data type;
(c) converting the revised mathematical expression incorporating the single-character revision into revised MathML of the mathematical expression, using the determined set of conversion rules;
(d) converting the revised MathML of the mathematical expression into one or more output math formats comprising at least one of braille math output or presentation markup math output; and (e) transmitting the revised mathematical expression, converted into the one or more output math formats to one or more output devices including at least one of the visual presentation devices or at least one refreshable braille display devices.

8. The method of claim 7, wherein the second set of data conversion rules for MathML to braille math output includes a plurality of braille encoding rules that do not correspond to character mapping rules, the plurality of braille encoding rules including at least one braille encoding rule calling for a multipurpose indicator braille symbol.

9. The method of claim 7, wherein the second set of data conversion rules for converting MathML to braille math output includes a braille encoding rule for handling nested fractions that does not correspond to a character mapping rule, and wherein the set of braille output characters includes a first braille symbol corresponding to a fraction indicator and a second braille symbol corresponding to a nested fraction indicator.

10. The method of claim 7, wherein converting the MathML representation of the mathematical expression to the set of braille output math characters using the second set of data conversion rules comprises:
applying character mapping rules to the MathML representation of the mathematical expression, to generate a corresponding string of braille characters;
analyzing the generated string of braille characters to detect one or more predetermined character patterns; and
using the at least one braille encoding rule that does not correspond to a character mapping rule, to convert the one or more predetermined characters patterns in the generated string of braille characters.

11. The method of claim 10, wherein detecting the one or more predetermined characters patterns, and using the at least one braille encoding rule that does not correspond to a character mapping rule to convert the predetermined characters patterns comprises:
determining that two consecutive characters in the generated string of braille characters correspond to a single mathematical symbol; and
inserting a designated indicator braille character in between the two consecutive characters, in response to determining that the two consecutive characters correspond to a single mathematical symbol.

12. The method of claim 7, wherein the set of braille output math characters includes a fraction indicator braille character that does not correspond to any character in the received input data, a fraction terminator braille character that does not correspond to any character in the received input data, and fraction bar braille character.

13. The method of claim 12, wherein the set of braille output math characters further includes a nested fraction indicator braille character that is separate from the fraction indicator braille character, and a nested fraction terminator braille character that is separate from the fraction terminator braille character.

14. The method of claim 7, wherein the set of braille output math characters includes a root indicator braille character, and a nested root indicator braille character that is separate from the root indicator braille character.

15. The method of claim 7, wherein converting the MathML representation of the mathematical expression to the set of braille output math characters using the second set of data conversion rules comprises:
identifying a first character corresponding to a subscript or superscript character in the MathML representation of the mathematical expression, and a second character in the MathML representation of the mathematical expression to which the first subscript or superscript character applies;
determining that the first subscript or superscript character is an integer; and
based on the determination that the first subscript or superscript character is an integer, applying an abbreviated braille encoding rule by which the first character, the second character, and the relationship between the first character and the second character is represented by only two braille characters.

16. A computer-program product tangibly embodied in a non-transitory machine-readable storage medium, including instructions configured to cause one or more data processors to perform actions including:
initiating a multi-user interactive math computing session including at least one refreshable braille display device and at least one visual presentation device;
receiving math input data representing a presentation markup representation of a mathematical expression during the multi-user interactive math computing session;
converting the math input data representing the presentation markup representation of the mathematical expression to a mathematical markup language (MathML) representation of the mathematical expression, using a first set of data conversion rules for converting presentation markup of mathematical expressions to MathML,
converting the MathML representation of the mathematical expression to a set of braille output math characters, using a second set of data conversion rules for converting MathML to braille math output, wherein the set of braille math output characters includes at least one braille mathematical symbol that does not correspond to any character in the received input data or in the MathML representation of the mathematical expression;
transmitting the set of braille output characters to the at least one refreshable braille display device, wherein the converting and transmitting of the braille math output characters is performed in real-time in response to the receiving the math input data representing the presentation markup representation of the mathematical expression; and
receiving a plurality of single-character revisions to the mathematical expression during the multi-user interactive math computing session, including at least a first single-character revision received as braille math input from the at least one refreshable braille display device, and a second single-character revision received as presentation markup math input from the at least one visual presentation device; and
in response to each of the plurality of single-character revisions to the mathematical expression received during the multi-user interactive math computing session;
(a) determining an input data type of the received single-character revision to the mathematical expression;
(b) determining a set of conversion rules for converting the revised mathematical expression to MathML, based on the determined input data type;
(c) converting the revised mathematical expression incorporating the single-character revision into revised MathML of the mathematical expression, using the determined set of conversion rules;

(d) converting the revised MathML of the mathematical expression into one or more output math formats comprising at least one of braille math output of presentation markup math output; and (e) transmitting the revised mathematical expression, converted into the one or more output math formats, to one or more output devices including at least one of the visual presentation devices or at least one refreshable braille display devices.

17. The computer-program product of claim 16, including further instructions configured to cause the one or more data processors to perform actions including:
    receiving a set of braille input characters from a first refreshable braille display device, the set of braille input characters representing an updated mathematical expression;
    retrieving a third set of data conversion rules for converting braille input to MathML; and
    converting the received braille input characters representing the updated mathematical expression to a MathML representation of the updated mathematical expression, using the third set of data conversion rules.

18. The computer-program product of claim 17, including further instructions configured to cause the one or more data processors to perform actions including:
    receiving a set of presentation markup characters from a first visual presentation device, the set of presentation markup characters representing an updated mathematical expression;
    converting the received presentation markup characters representing the updated mathematical expression to a MathML representation of the updated mathematical expression, using the first set of data conversion rules,
    converting the MathML representation of the updated mathematical expression back to a presentation markup representation of the updated mathematical expression, using a third set of data conversion rules; and
    transmitting the presentation markup representation of the updated mathematical expression to the identified one or more visual presentation devices, wherein the converting and transmitting of the presentation markup representation of the updated mathematical expression is performed in real-time in response to the receiving the set of braille input characters.

* * * * *